(12) United States Patent
Kadaba et al.

(10) Patent No.: US 12,076,252 B2
(45) Date of Patent: Sep. 3, 2024

(54) LORDOTIC INTERVERTEBRAL SPACER WITH RATCHET LOCKING MECHANISM AND INTEGRAL EXPANSION MECHANISM

(71) Applicant: Ingeniumspine, LLC, Phoenix, AZ (US)

(72) Inventors: Murali Kadaba, Austin, TX (US); Damien Shulock, San Francisco, CA (US); B. Thomas Barker, Bartlett, TN (US); Dennis Crandall, Mesa, AZ (US); Jason Datta, Phoenix, AZ (US)

(73) Assignee: Ingeniumspine, LLC, Phoenix, AZ (US)

( * ) Notice: Subject to any disclaimer, the term of this patent is extended or adjusted under 35 U.S.C. 154(b) by 0 days.

(21) Appl. No.: 18/223,497

(22) Filed: Jul. 18, 2023

(65) Prior Publication Data

US 2024/0225854 A1    Jul. 11, 2024

Related U.S. Application Data

(63) Continuation-in-part of application No. 18/215,072, filed on Jun. 27, 2023, now Pat. No. 12,011,370.

(60) Provisional application No. 63/390,945, filed on Jul. 20, 2022, provisional application No. 63/357,411, filed on Jun. 30, 2022.

(51) Int. Cl.
*A61F 2/44*  (2006.01)
*A61F 2/46*  (2006.01)
*A61F 2/30*  (2006.01)

(52) U.S. Cl.
CPC .... *A61F 2/447* (2013.01); *A61F 2002/30481* (2013.01); *A61F 2002/30579* (2013.01)

(58) Field of Classification Search
CPC .......... A61F 2/447; A61F 2/44; A61F 2/4611; A61F 2002/30481; A61F 2002/30579
USPC .............................................. 623/17.11–17.16
See application file for complete search history.

(56) References Cited

U.S. PATENT DOCUMENTS

| | | | |
|---|---|---|---|
| 6,159,244 A * | 12/2000 | Suddaby | A61F 2/4611 606/247 |
| 6,491,724 B1 | 12/2002 | Ferree | |
| 6,562,074 B2 * | 5/2003 | Gerbec | A61F 2/4611 623/17.15 |
| 8,828,085 B1 * | 9/2014 | Jensen | A61F 2/447 623/17.11 |
| 9,364,344 B2 * | 6/2016 | Whipple | A61F 2/4455 |
| 9,539,109 B2 * | 1/2017 | Spangler | A61L 31/005 |

(Continued)

*Primary Examiner* — Jessica Weiss
(74) *Attorney, Agent, or Firm* — Etherton Law Group, LLC

(57) ABSTRACT

An expandable intervertebral spacer system having a cage formed by a top plate and a bottom plate which are held apart a changeable distance. An expansion mechanism within the cavity is configured to force the top plate apart from the bottom plate a desired distance. One expansion mechanism is an expansion spring that is held in a compressed state with a removable trigger wire that temporarily secures the top and bottom plates together. Once the spacer is implanted in a patient, the trigger wire is removed permitting the expansion spring to relax, in a single motion, to the farthest extent possible in an intervertebral space. The top plate and the bottom plate are locked apart using a locking mechanism made of two saw-toothed posts that cooperate to lock the top plate a desired distance from the bottom plate. The sawtooth posts are biased against each other with a spring.

21 Claims, 20 Drawing Sheets

(56) References Cited

U.S. PATENT DOCUMENTS

| | | | |
|---|---|---|---|
| 10,729,553 B2 * | 8/2020 | Bell | A61F 2/4455 |
| 10,729,554 B2 * | 8/2020 | Bootwala | A61F 2/4455 |
| 11,234,833 B2 * | 2/2022 | Brotman | A61F 2/4455 |
| 2007/0123987 A1 * | 5/2007 | Bernstein | A61F 2/44 623/17.11 |
| 2010/0137987 A1 * | 6/2010 | Diao | A61B 17/8852 623/17.11 |
| 2014/0188225 A1 * | 7/2014 | Dmuschewsky | A61F 2/442 623/17.16 |
| 2014/0343678 A1 * | 11/2014 | Suddaby | A61F 2/4611 623/17.16 |
| 2019/0053912 A1 * | 2/2019 | Suddaby | A61F 2/447 |
| 2021/0030562 A1 * | 2/2021 | Suddaby | A61F 2/447 |

* cited by examiner

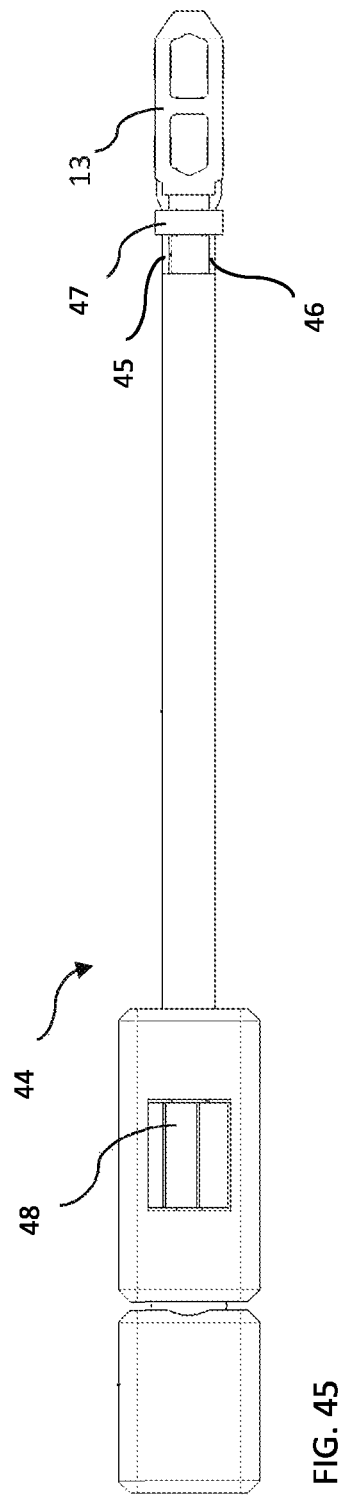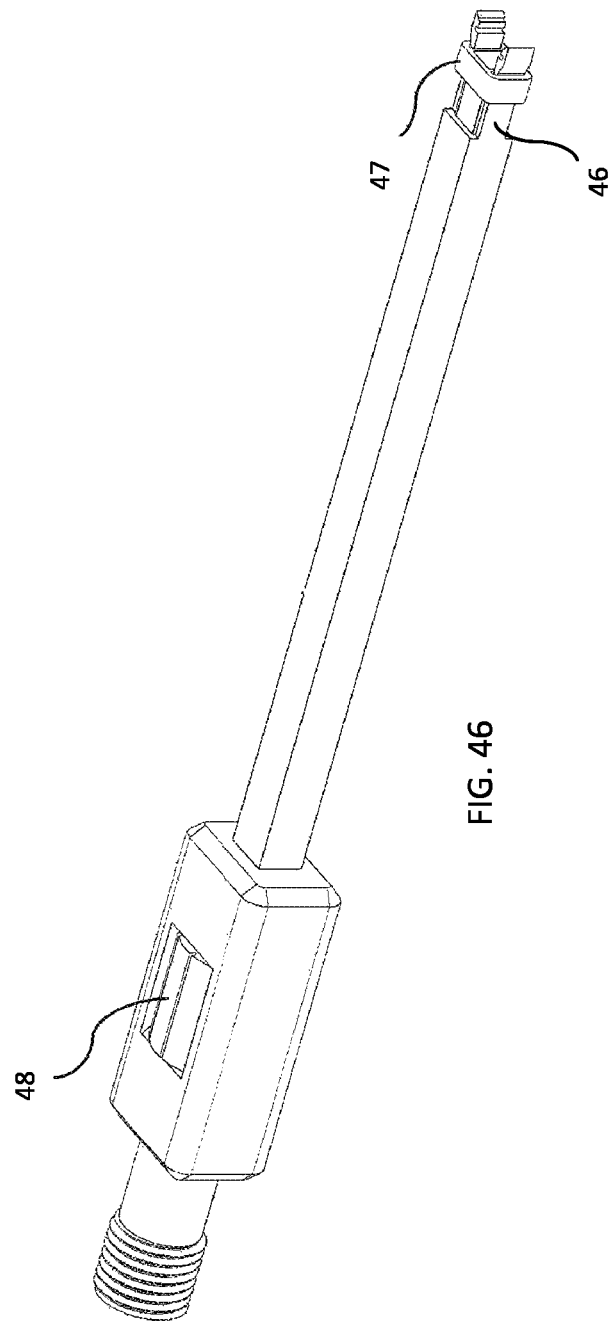

LORDOTIC INTERVERTEBRAL SPACER WITH RATCHET LOCKING MECHANISM AND INTEGRAL EXPANSION MECHANISM

CROSS-REFERENCE TO RELATED APPLICATIONS

This application claims the benefit of U.S. Provisional Application No. 63/390,945 filed Jul. 20, 2022, which is incorporated herein by reference. This application is a continuation-in-part of U.S. application Ser. No. 18/215,072 filed Jun. 27, 2023, which claims the benefit of U.S. Application No. 63/357,411 filed Jun. 30, 2022, both of which are incorporated herein by reference.

FIELD OF INVENTION

The present invention relates generally to spacers for orthopedic surgery of the spine. The present invention relates particularly to implants that are placed within an intervertebral disc space which have a ratchet-like locking mechanism with steps and an integral expansion mechanism.

BACKGROUND

Interbody fusion is a type of spine surgery that removes all or part of a degenerated disc from between two adjacent vertebrae in a patient's back. Once the disk is removed, an expandable device is inserted into the disc space between the adjacent vertebrae to forcibly space the vertebrae apart and maintain intervertebral separation. Cancellous bone graft material is packed in and around the spacer to provide a scaffolding so that new bone can be formed. During healing the adjacent vertebra fuse into a single monolithic structure. The more graft material used, and the more surface area it has touching the patient's bone, the more likely the fusion will be successful. Therefore, it is advantageous for the inserted device to have a large, open cage structure to receive and expose the bone graft material.

Typically, the spacer is expanded by using a removable mated tool that engages an expansion mechanism that resides within the body of the spacer. The user uses the tool to incrementally expand the spacer to a proper height to keep the vertebra separated a desired distance. After the spacer is expanded to the proper height, the expansion tool is removed. If a spacer is expanded too far, often the spacer is simply removed and a new one inserted, wasting the original spacer. It would be desirable to have a spacer that expands to the proper height automatically, without the user having to incrementally expand the spacer.

Lordosis refers to curvature of the spine that is posteriorly concave. A certain amount of curvature is desired for spine health and patient comfort, but too little curvature or too much curvature may be problematic. When implanting a device between two vertebrae, the lordosis angle of the disk space being repaired must be set appropriately not only for the two surrounding vertebrae, but for vertebrae adjacent to those which may be consequently affected. It would be desirable to have an expandable intervertebral implant to achieve a desired lordosis angle.

Once expanded, it is desirable to lock the spacer at the desired height and angle. The locking mechanism must be strong enough to withstand the compressive forces between the vertebrae and the cage must be robust enough so that it does not collapse or otherwise fail during the patient's lifetime. Strength and durability are vitally important, but making a spacer needlessly robust detracts from the size of the cavity in the spacer for holding bone graft material. A balance is desired.

It is an object of this invention to provide an expandable lordotic interbody spacer with an integral expansion mechanism and strong and durable locking mechanism with steps. It is another object of this invention to provide an expandable lordotic interbody spacer that expands to the proper height automatically. It is another object of this invention to provide an expandable lordotic interbody spacer and a robust locking mechanism that can be expanded to a desired lordosis angle, whether expanded automatically or by the user with a mated expansion tool.

SUMMARY OF THE INVENTION

An expandable intervertebral spacer comprises a top plate and a bottom plate that are connected together with one or more stanchions that lock the plates apart a desired distance. Each stanchion is made of two saw-toothed posts that cooperate to lock the top plate a desired distance from the bottom plate with a ratchet-like locking mechanism. The saw-tooth posts are biased against each other with a spring. Optionally, each stanchion is surrounded by a sheath to prevent bone particles and other debris from interfering with the mating of the saw teeth.

One or more expansion springs is disposed between the top plate and bottom plate. As the spacer is inserted into the patient, each expansion spring is held in a compressed state with a removable trigger wire or pin that temporarily secures the top and bottom plates together. Once the spacer is implanted in a patient, the trigger wire is removed permitting each expansion spring to instantly relax to the farthest extent possible in the intervertebral space until the top plate is pushing on the top vertebrae and the bottom plate is pushing on the bottom vertebrae. In this way that the plates are automatically separated the proper height in a single motion, without the user having to separate the plates incrementally.

In some embodiments two compressed expansion springs are disposed between the top and bottom plates and, when the expansion springs relax, the top plate is forced against the top vertebrae. Once the expansion springs come to rest, the top plate is likely to remain substantially parallel to the bottom plate, but in some cases the top plate may be tilted relative to the bottom plate as the top plate meets an uneven surface on the vertebrae above the spacer.

In other embodiments a single compressed expansion spring is disposed between the top and bottom plates at the distal end of the spacer and the plates are connected together at the proximal end with a hinge. When the expansion spring relaxes, the distal end of the spacer is forced against the top vertebrae, forming the spacer into a wedge shape between the distal and proximal ends of the spacer.

In other embodiments, the plates are connected together at the proximal end with a hinge and forced open with a mechanical expansion mechanism using a removable expansion tool.

BRIEF DESCRIPTION OF THE DRAWINGS

FIG. 45 is a top view of an insertion tool.

FIG. 46 is a perspective partial view of the insertion tool of FIG. 45.

DETAILED DESCRIPTION OF THE INVENTION

Figure 1:
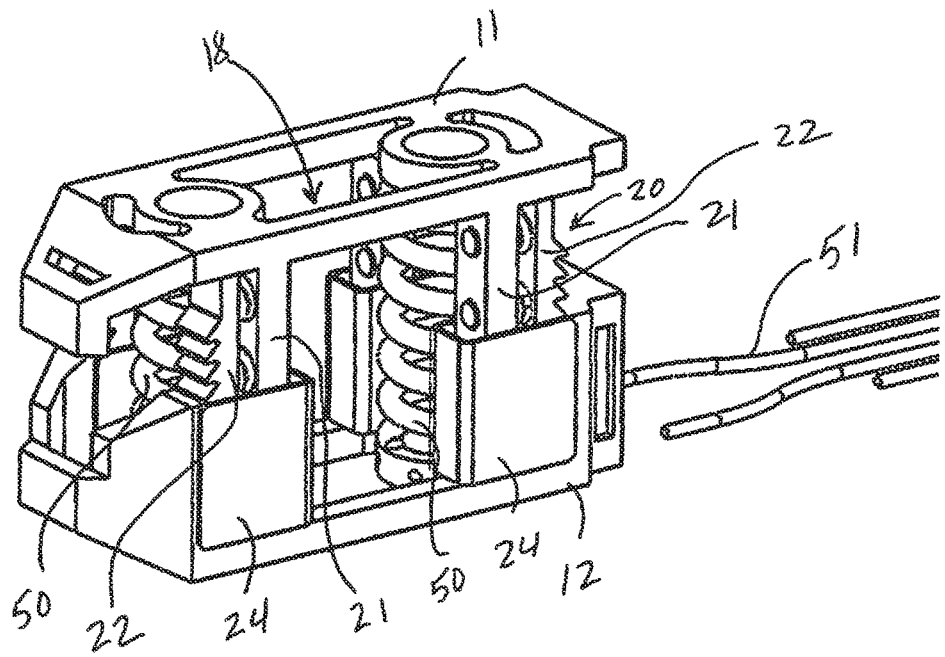
FIG. 1 is a top perspective view of a first embodiment of a spacer in an expanded position and its trigger wire removed from the device
Figure 2:
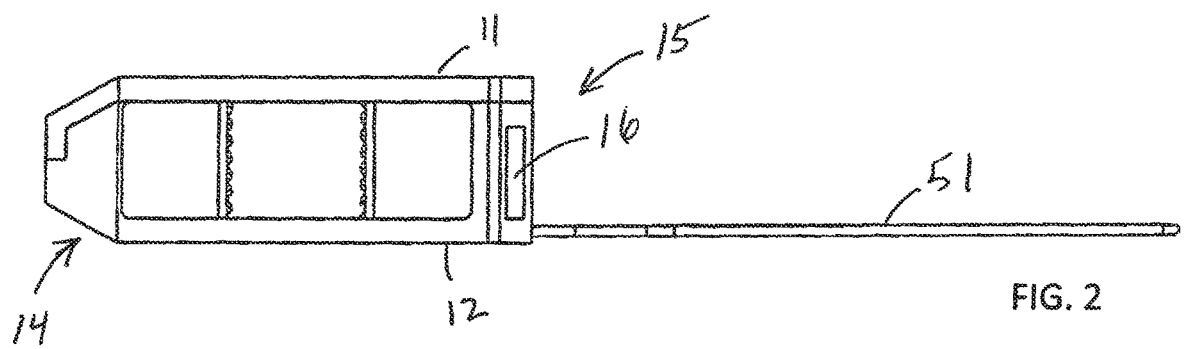
FIG. 2 is a side view of the spacer of FIG. 1 in an unexpanded position and its trigger wire installed in the device.
Figure 3:
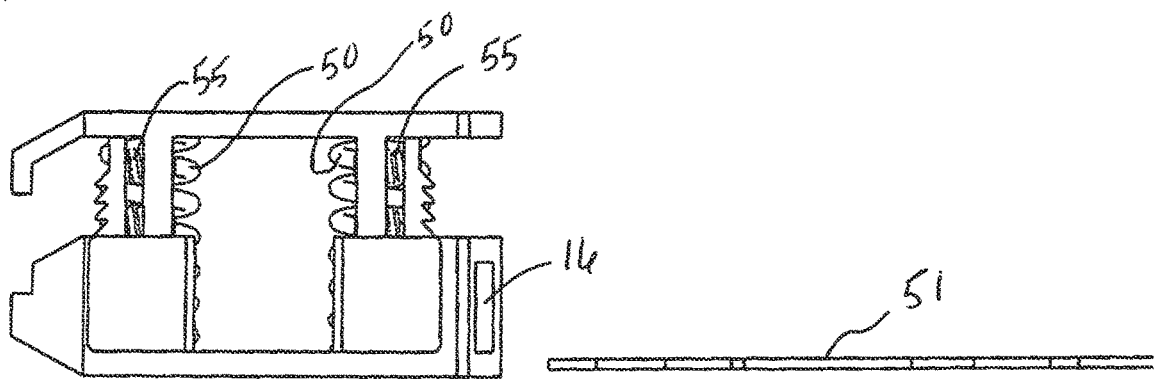
FIG. 3 is a side view of the spacer of FIG. 1 in an unexpanded position and its trigger wire removed from the device.
Figure 4:
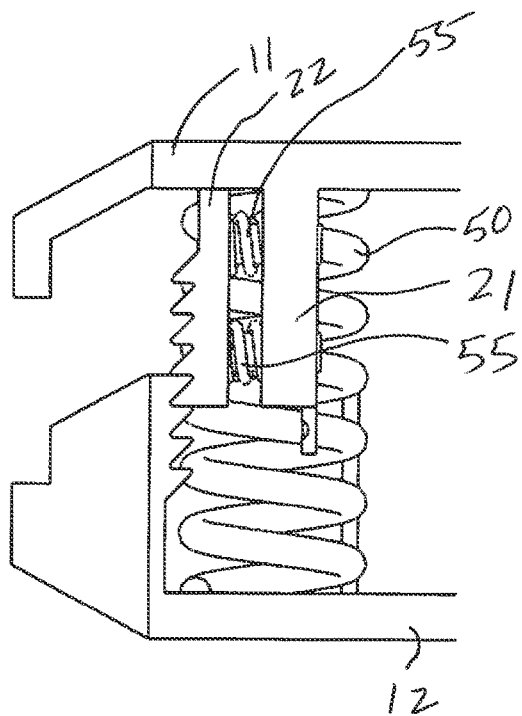
FIG. 4 is a partial side view of the spacer of FIG. 1.
Figure 5:
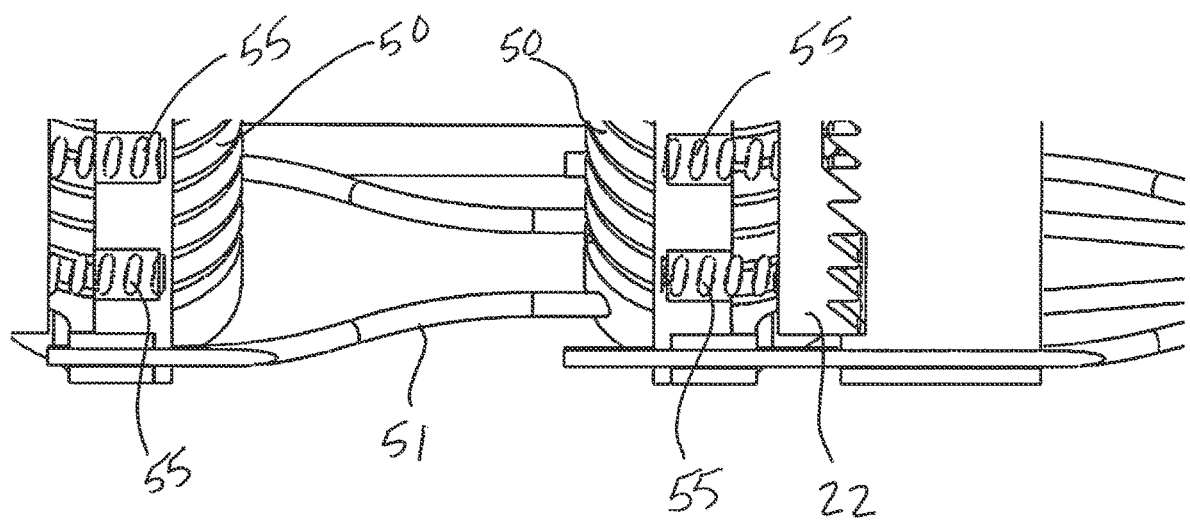
FIG. 5 is a partial side perspective view of the spacer of FIG. 1 showing the trigger wires that lock the expansion springs in closed position.
Figure 6:
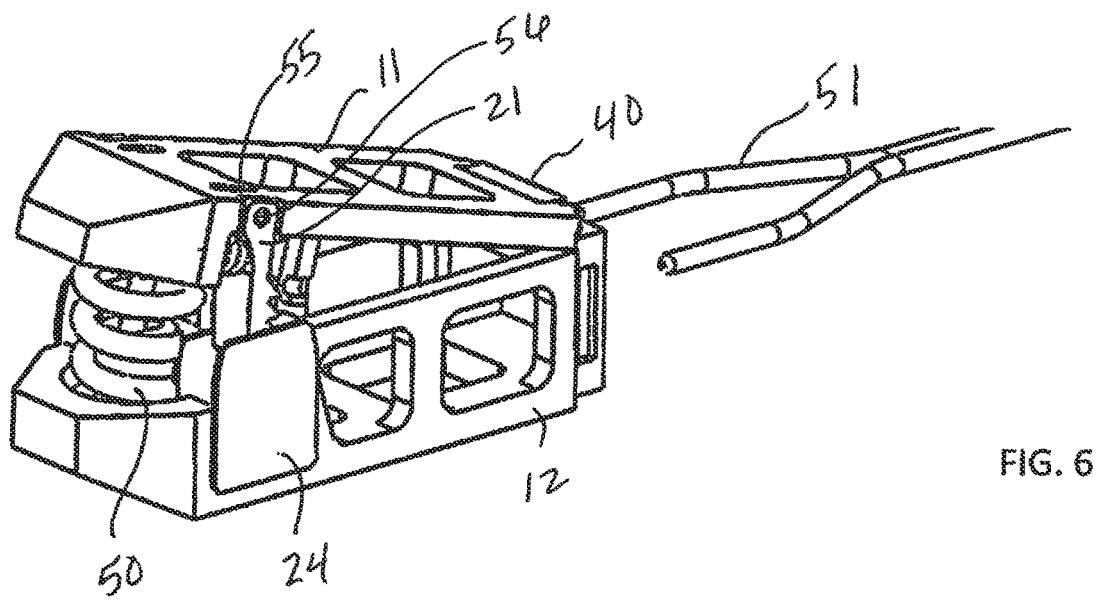
FIG. 6 is a top perspective view of a second embodiment of a spacer in an expanded position and its trigger wire removed from the device.
Figure 7:
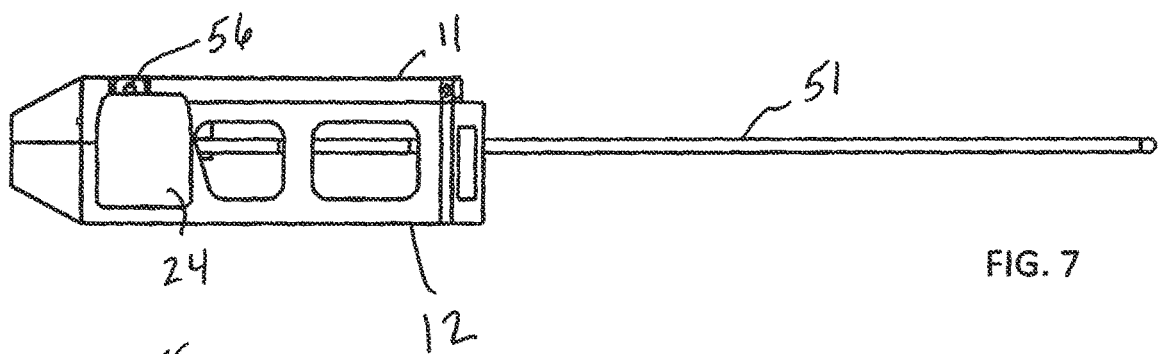
FIG. 7 is a side view of the spacer of FIG. 6 in an unexpanded position and its trigger wire installed in the device.
Figure 8:
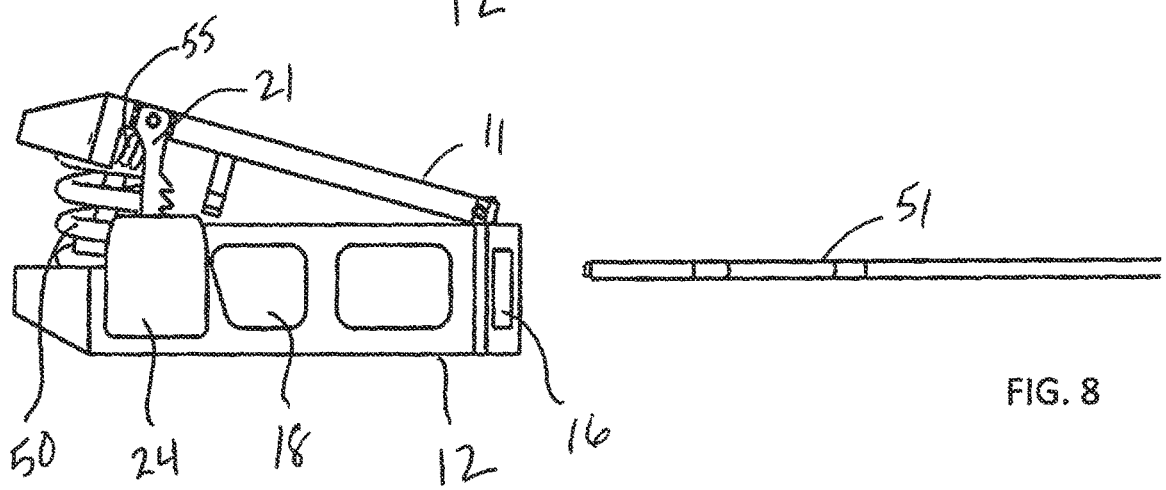
FIG. 8 is a side view of the spacer of FIG. 6 in an expanded position and its trigger wire removed from the device.
Figure 9:
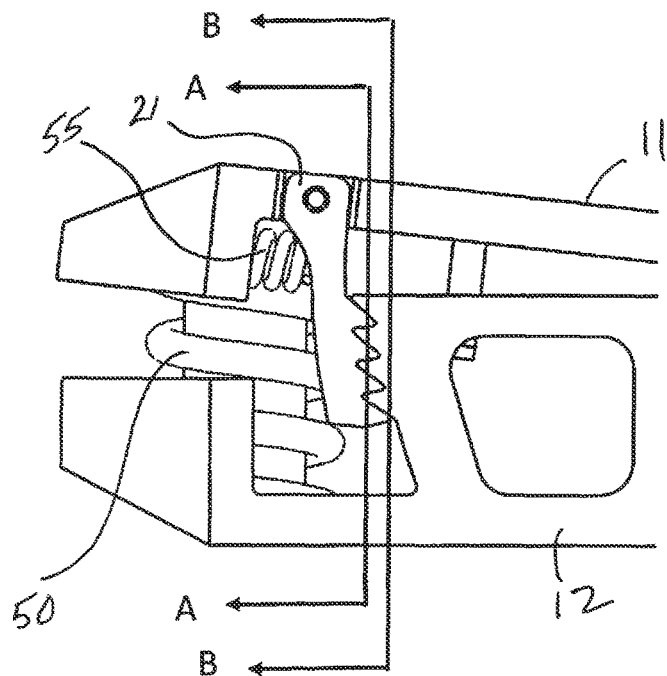
FIG. 9 is a partial side view of the spacer of FIG. 6 without the sheaths that cover the locking mechanism, in a partially expanded position.
Figure 10:
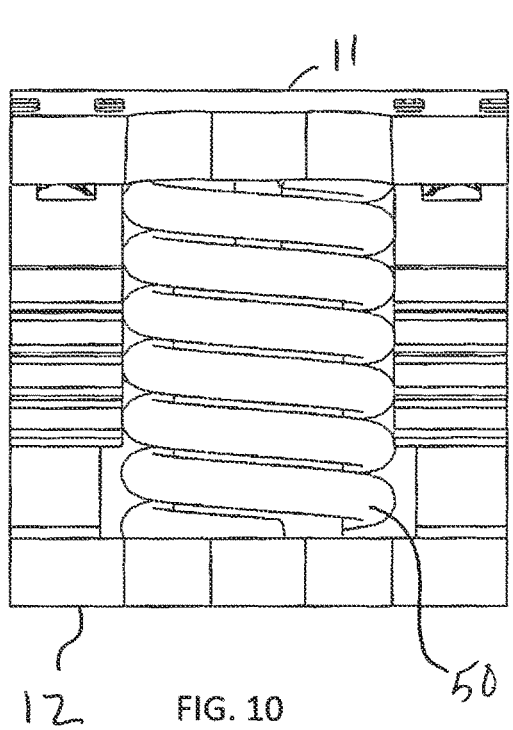
FIG. 10 is a cross-section view of the spacer of FIG. 6 along line A-A of FIG. 9.
Figure 11:
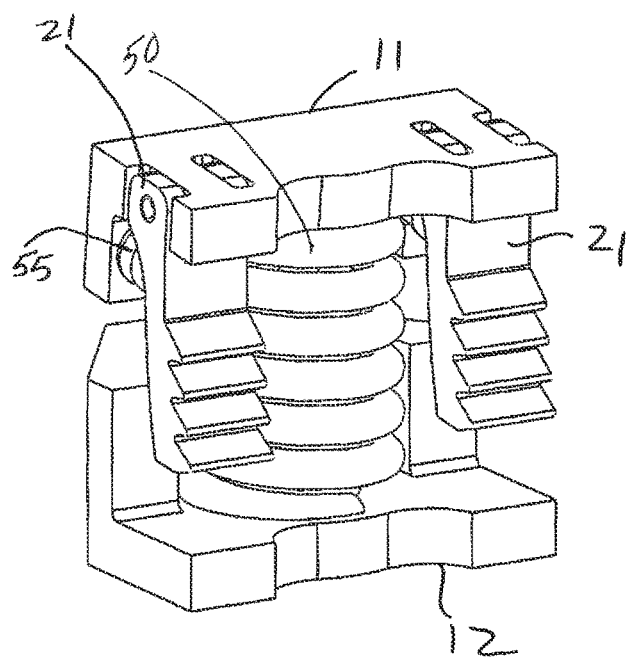
FIG. 11 is a side-perspective view of the spacer of FIG. 10.
Figure 12:
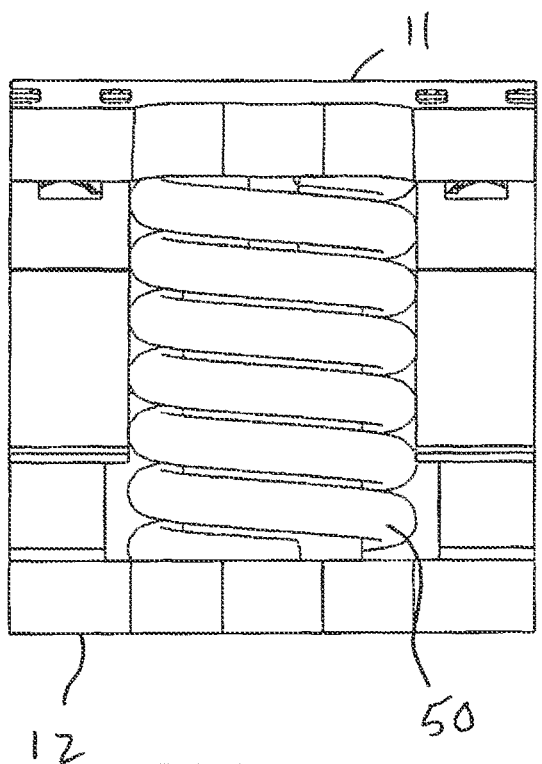
FIG. 12 is a cross-section view of the spacer of FIG. 6 along line B-B of FIG. 9.
Figure 13:
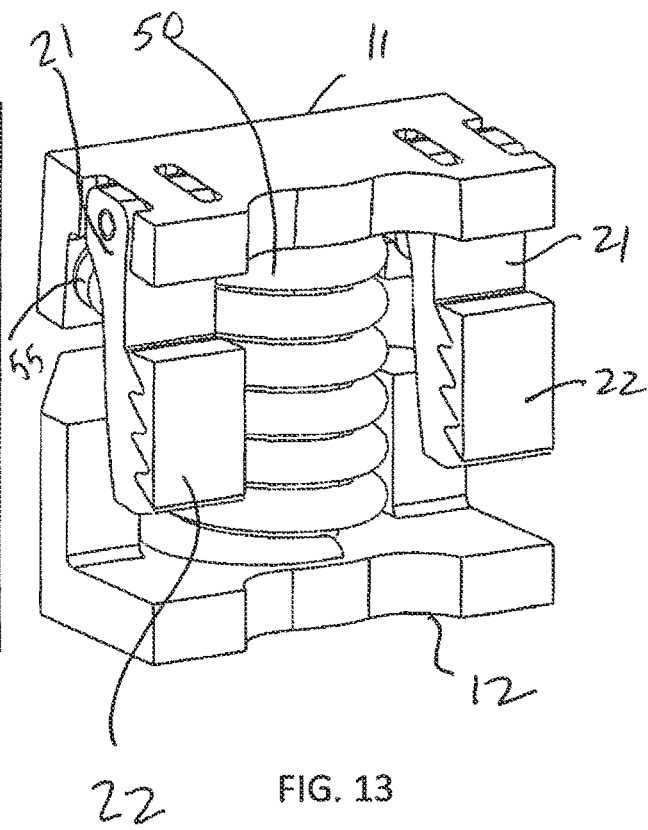
FIG. 13 is a side-perspective view of the spacer of FIG. 12.

This expandable intervertebral spacer comprises a spacer body 10 comprising a top plate 11 and a bottom plate 12, and an integral locking mechanism that separates the plates and holds them apart at a desired distance. The locking mechanism comprises one or more stanchions 20, each comprising two saw-tooth posts that move relative to one another. To expand the spacer, the top and bottom plates are forced apart using an expansion mechanism that is within the spacer body.

The top plate 11 and bottom plate 12 of the spacer body cooperate to form an open-sided, substantially rectangular cage 13 surrounding a cavity 17. The cage has a top, a bottom, and four sides. The cage has a distal end and a proximal end that correlate to the distal and proximal ends of the spacer body. The portions of the plates forming the cage 13 are generally shaped as squares or rectangles with rounded corners. See for example FIGS. 1, 6, 14, 22, and 28. Instead of continuous solid sheets of material, each of the four sides of the cage 13 has cutouts 18 to permit bone graft material to be more easily packed into the cavity 17 between the plates and increase the surface exposure of the graft material to the patient's vertebrae.

Figure 36:
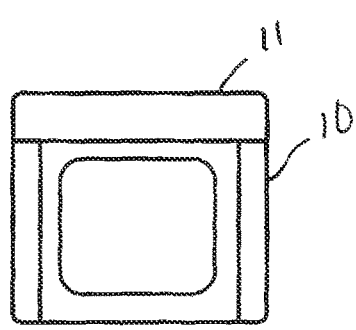
FIG. 36 is an end view of the spacer of FIG. 1 showing the opening for the insertion tool.
Figure 37:
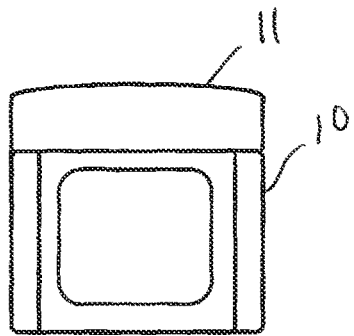
FIG. 37 is an end view of a first alternative embodiment of the spacer of FIG. 1 having a convex top, showing the opening for the insertion tool.
Figure 38:
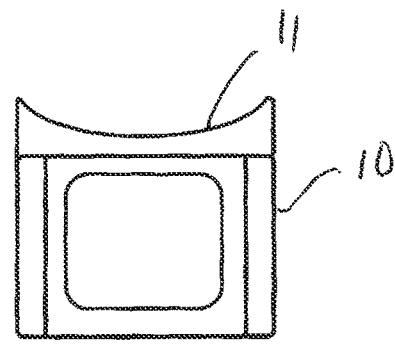
FIG. 38 is an end view of a second embodiment of the spacer of FIG. 1 having a concave top, showing the opening for the insertion tool.

Although the general shape of vertebrae 9 are common between patients, the specific size, shape, lordosis, and condition of the cancellous bone are peculiar to each patient. These biological factors affect the size, shape and placement of the spacer. Each of the top or bottom plate may be flat, concave or convex, depending on the shape needed to most closely match the curvature of the surfaces of the patient's vertebrae. See FIGS. 36-38.

The spacer is inserted into the patient's body in an unexpanded form using a removable insertion tool 44. The insertion tool 44 has clamping arms 45 and 45 that mate with clamping slots 16 on the proximal end 15 of the spacer body. See FIGS. 45-46. The ends of the clamping arms are tabs that fit in the clamp slots 16 on the proximal end of the spacer body so that the insertion tool can securely hold on to the spacer body during insertion and release it once inserted. The clamp arm tabs are inserted into the clamp slots 16, and the tabs are closed toward each other by moving the clamp collar 47 toward the end of the clamp arms. The clamp collar 47 is moved over the clamp arms by rotating a threaded cylinder 48. Rotation of the cylinder 48 in a first direction moves the collar 47 toward the spacer body, tightening the tabs in the clamp slots 16 of the spacer body. Rotation of the cylinder 48 in the reverse direction moves the collar 47 away from the cage, loosening the tabs from the slots of the cage.

Figure 43:
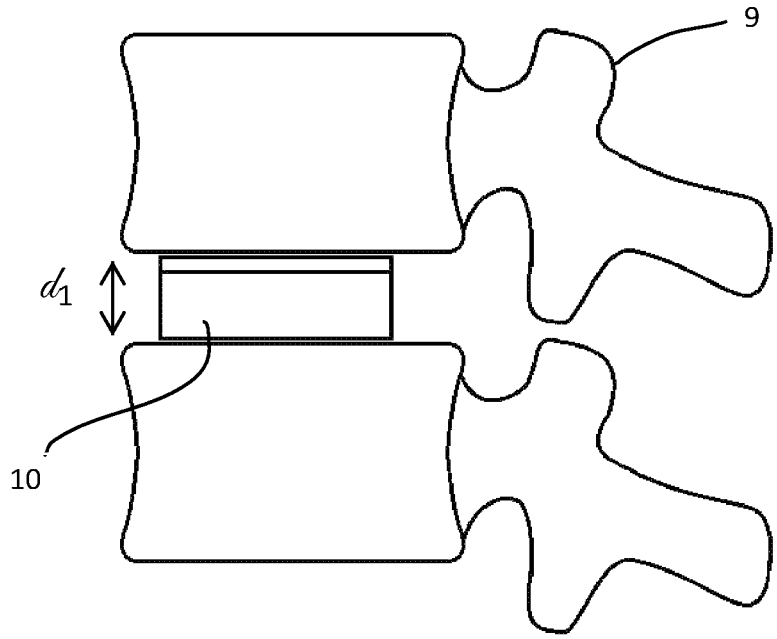
FIG. 43 is a schematic illustration of an unexpanded hinged spacer between two vertebrae.
Figure 44:
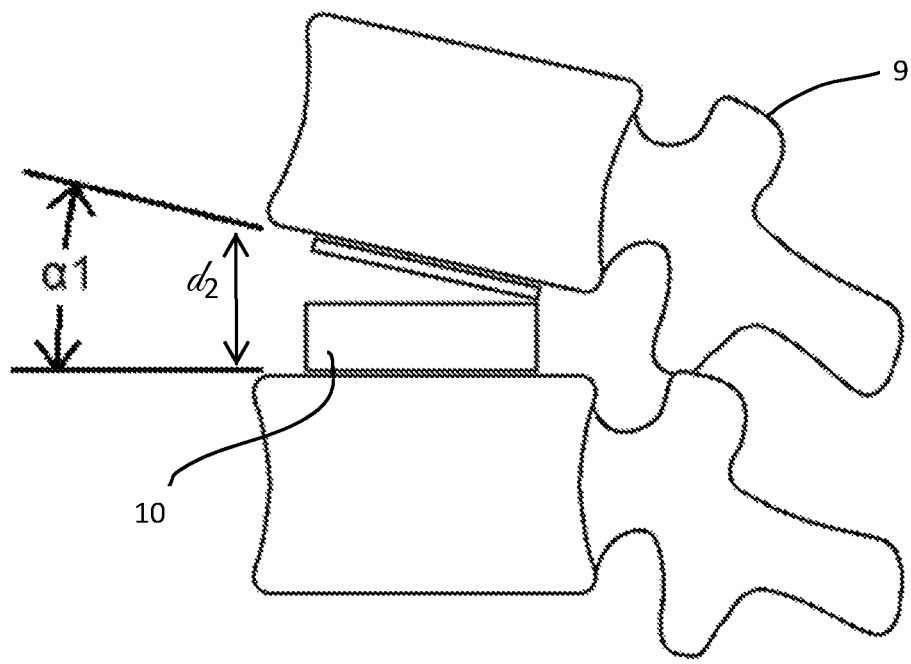
FIG. 44 is a schematic illustration of an expanded hinged spacer between two vertebrae.

FIG. 43 shows a single unexpanded spacer body inserted between two vertebrae 9 which are separated by a distance $d_1$. FIG. 44 shows that single spacer body expanded between the two vertebrae 9, forcing the vertebrae 9 apart a distance $d_2$ and angle $\alpha 1$. The distal end 14 of the spacer body is the leading end when inserting the device between vertebrae and is typically rounded for ease of insertion. The distal end 14 is typically solid so that no debris from the patient's body enters the cavity 17 during insertion, but optionally the distal end 14 may also have cutouts. The proximal end 15 of the spacer body is an open end to accommodate the insertion tool.

Figure 14:
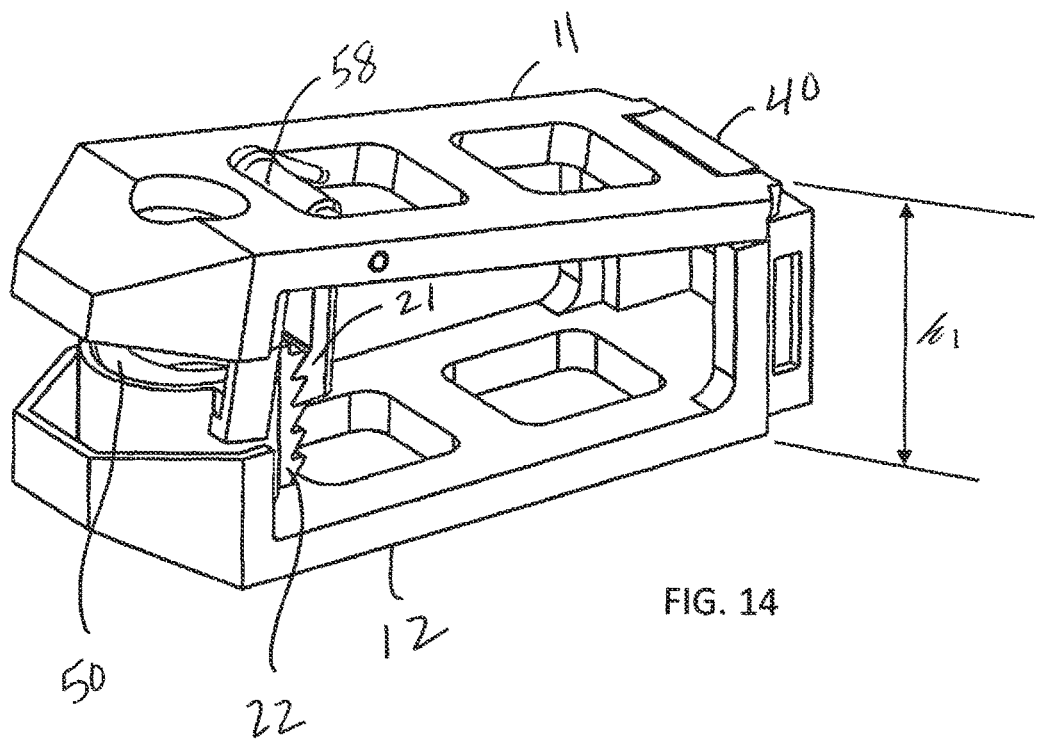
FIG. 14 is a top perspective view of a third embodiment of a spacer in an expanded position.
Figure 15:
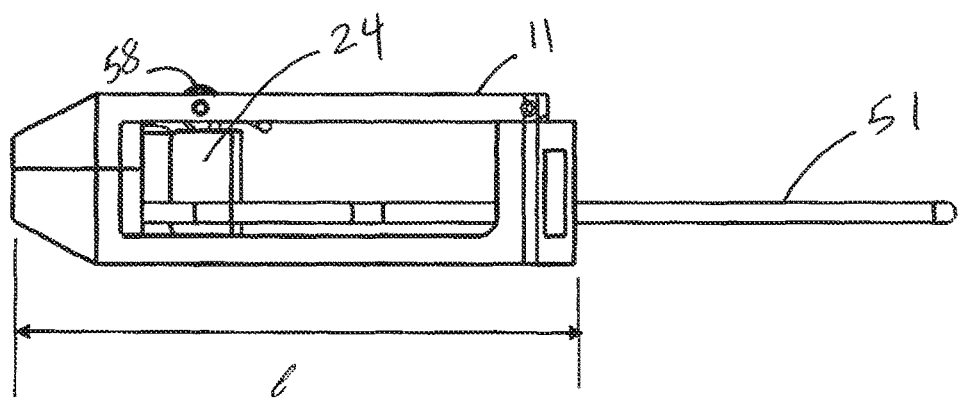
FIG. 15 is a side view of the spacer of FIG. 14 in an unexpanded position and its trigger wire installed in the device.
Figure 16:
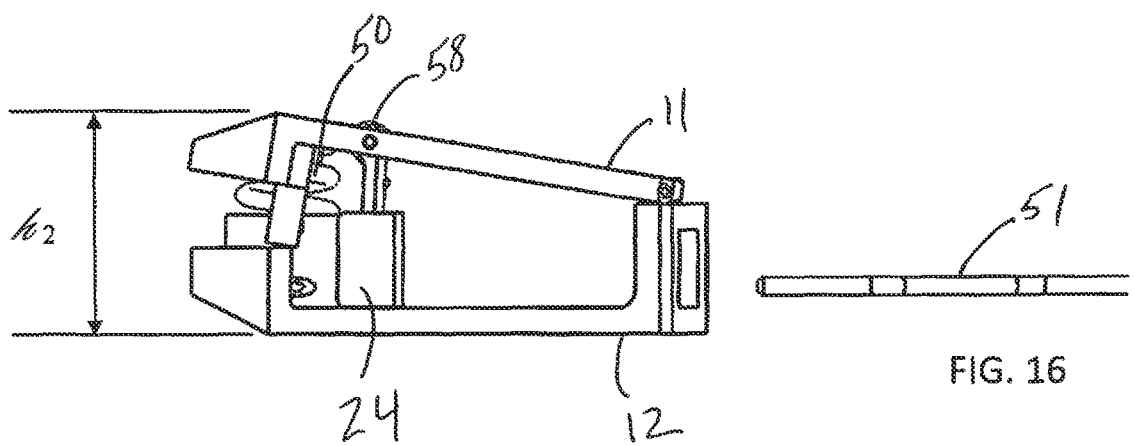
FIG. 16 is a side view of the spacer of FIG. 14 in an expanded position and its trigger wire removed from the device.
Figure 17:
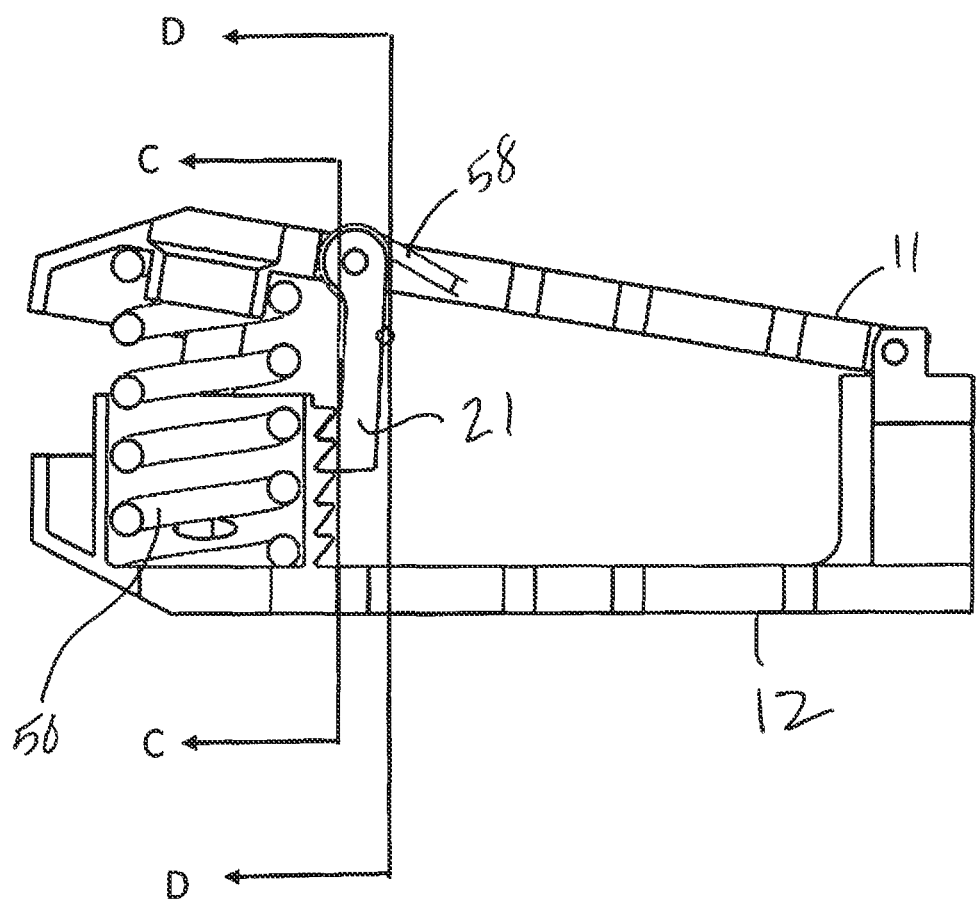
FIG. 17 is a cross-sectional view of the spacer of FIG. 14 without the sheaths that cover the locking mechanism, in a partially expanded position.
Figure 18:
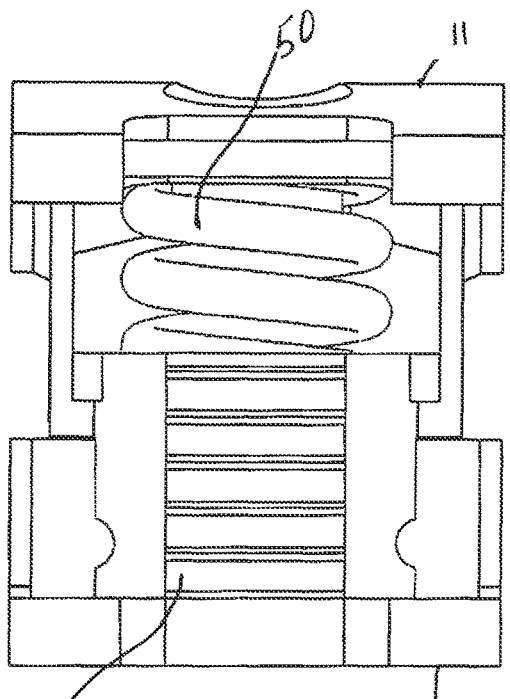
FIG. 18 is a cross-section view of the spacer of FIG. 14 along line C-C of FIG. 17.

The spacer is made of a biocompatible material, typically titanium or titanium alloy, and may be made in several sizes. They are typically between 26-30 mm long and 10-11 mm wide. Table 1 shows an exemplary range of sizes, where the height h of the spacer, the width w, and the length l, are shown in FIGS. 14 and 15.

TABLE 1

| Unexpanded Height $h_1$ (mm) | Fully expanded height $h_2$ (mm) at distal end | Angle formed | Width w (mm) | Length l (mm) |
| --- | --- | --- | --- | --- |
| 7 | 10 | 0-16 | 10 | 28 |
| 8 | 12 | 0-16 | 10 | 28 |
| 9 | 14 | 0-16 | 10 | 28 |
| 10 | 16 | 0-16 | 10 | 28 |
| 11 | 18 | 0-16 | 10 | 28 |
| 12 | 20 | 0-16 | 10 | 28 |

The top and bottom plates 11, 12 are separated and held apart by a locking mechanism that is integral with the device and disposed within the spacer body. The locking mechanism uses at least one stanchion 20 to provide robust and balanced support between the plates. Each stanchion 20 comprises two saw-tooth posts that move relative to one another and cooperate to lock the top plate a desired distance from the bottom plate. One post is stationary and preferably extends into the cage from the bottom plate. The other post is movable and preferably extends into the cage from the top plate. The posts are forced apart when the top and bottom plates are forced away from each other with the expansion mechanism, due to the cooperative shape of the saw teeth.

Figure 39:
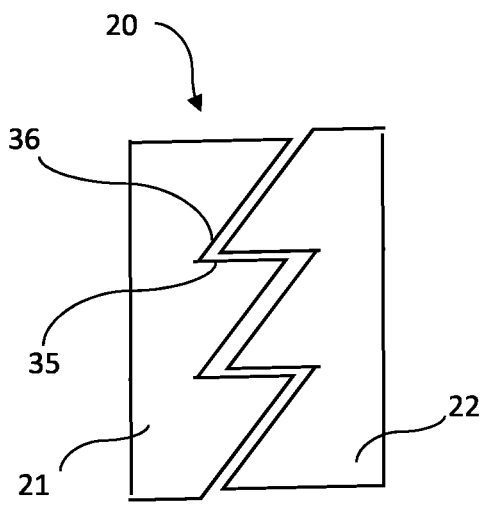
FIG. 39 is a schematic illustration of a portion of a stanchion.
Figure 40A:
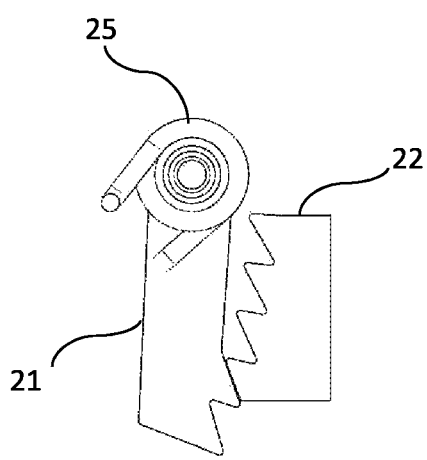
FIGS. 40A-D are side views of the locking mechanism, each with different number of saw-teeth engaged.
Figure 40B:
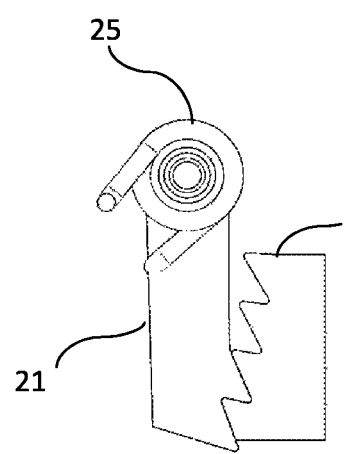
Figure 40C:
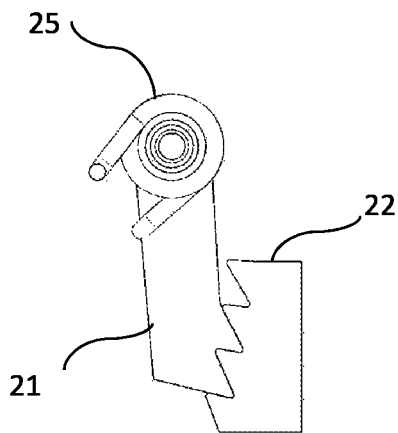
Figure 40D:
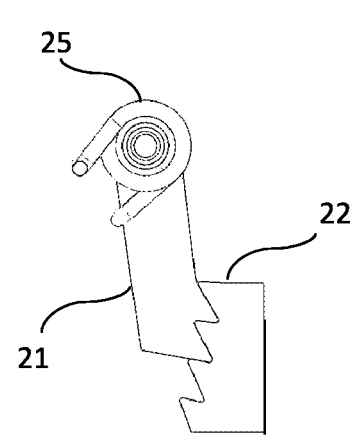
Figure 41:
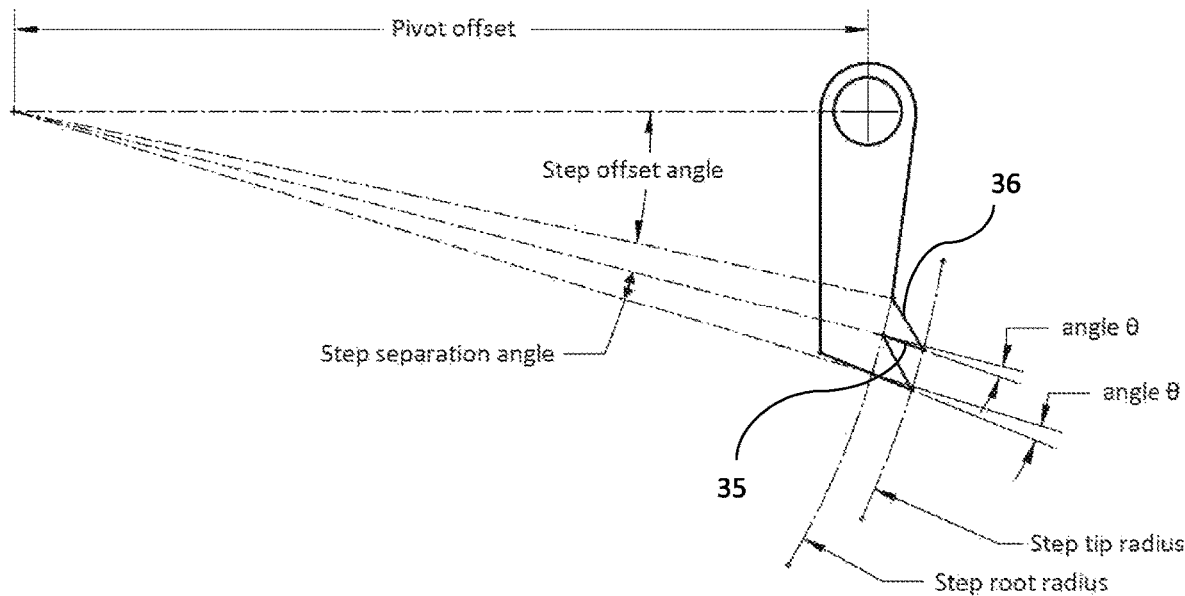
FIG. 41 illustrates effect of saw teeth that are not at 90 degrees to the post.
Figure 42:
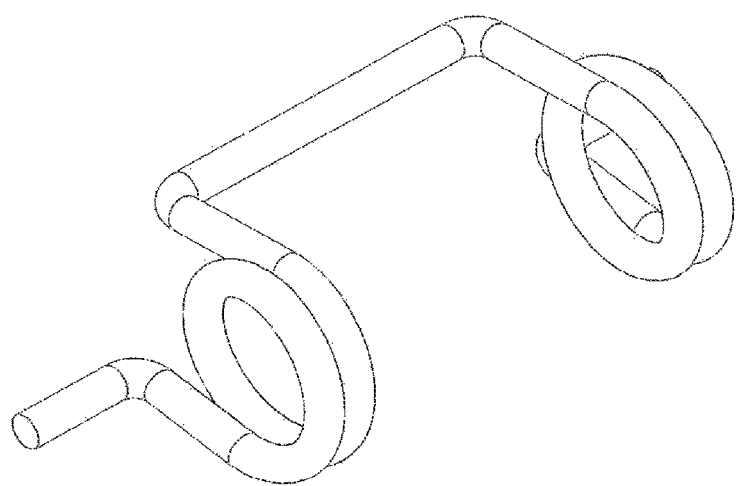
FIG. 42 is a perspective view of a torsion spring.

Each saw tooth is generally triangular with one side of the triangle extending away from the post at an angle of about 90-106 degrees. This portion of the tooth is referred to herein as the horizontal edge 35. In one embodiment, the horizontal edge is at a right angle to its post, parallel to the top and bottom plates 11, 12. See FIG. 39. In another embodiment, the horizontal edge is greater than 90 degrees to the post, and angle theta shows the difference from perpendicular. Angle theta denotes an angular offset from the line between the center-to-root line and root-to-tip line, where the root is the point at which the step attaches to the post. See FIG. 41. The other edge of the saw tooth is at a complementary angle to its post, referred to herein as the angled edge 36. The teeth of one post intermesh with the teeth of the neighboring post. When the saw teeth are engaged, the horizontal edge 35 of each tooth sits against a horizontal edge 35 of one or more teeth on the opposing post. This holds the top and bottom plates stationary relative to each other, locking the plates to each other. The greater the angle theta of the horizontal edge 35 to the post, the greater the force required to separate the posts 21, 22 from each other. When expanding the cage with horizontal edge at angles more than 90 degrees, the ramp has to be forced open farther than if the horizontal edge is at 90 degrees to get over the lip of the step. Then, the post slides down so that the teeth intermesh. Posts intermeshed with theta angles greater than zero create an interlocking force on the steps which pushes them together and increases the security of the locking mechanism.

The asymmetrical shape of the saw teeth enables the plates to be forced apart incrementally, one saw tooth at a time, in a ratchet-like motion. The posts 21, 22 are forced apart from each other when the top and bottom plates are forced away from each other with the expansion mechanism, due to the cooperative shape of the saw teeth. As the top plate is forced away from the bottom plate, as explained in more detail below, the angled edges of the teeth of the top post slide against the angled edges of the teeth of the bottom post, forcing the top post to rotate away from the bottom post in an amount sufficient to release the horizontal edges of the formerly intermeshed teeth.

The height of the saw teeth determines the distance of each increment of separation between the plates: the smaller the tooth height, the finer the degree of separation for each increment. The number of teeth and height of the teeth determine the maximum distance the plates can be separated. At maximum expansion, preferably a minimum of two teeth are engaged on each stanchion.

The width of the stanchion varies depending on the embodiment from about 2 mm-6 mm. FIGS. 6-13 show an embodiment with two stanchions. Assuming the horizontal edge 35 of the saw tooth is 2 mm wide and 1.5 mm deep. Assuming two teeth are engaged per stanchion, this provides for a minimum total contact area of 12 $mm^2$ (2 teeth×2 stanchions×1.5 mm wide×2 mm deep). Given a compressive strength of titanium alloy to be 850 MPA, the load to failure is 10,200 N.

Optionally, a sheath 24 surrounds each stanchion or the whole locking mechanism to prevent bone particles and other debris from interfering with the mating of the saw teeth. The sidewall thickness of the sheath 24 is preferably less than 1 mm.

Figure 47:
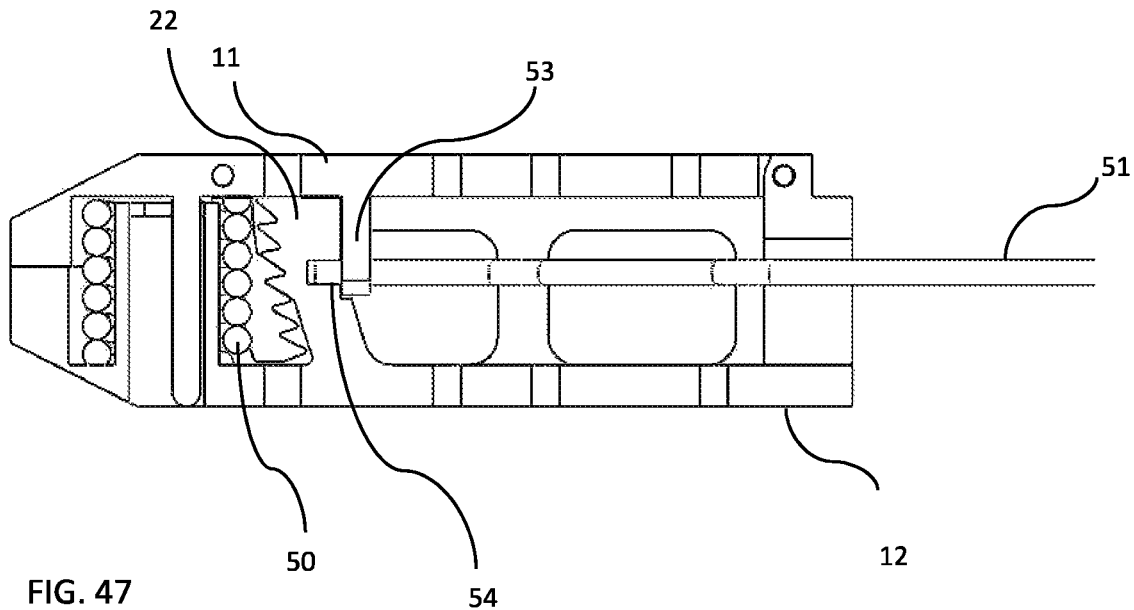
FIG. 47 is a cross-sectional view of the spacer of FIG. 7 showing the trigger wire in place.
Figure 48:
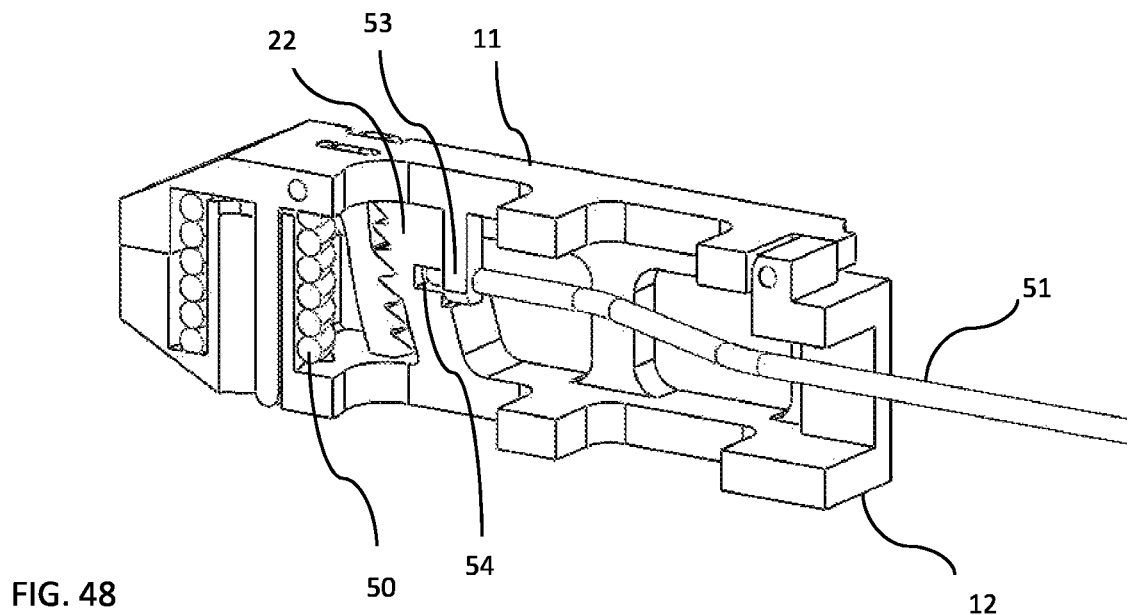
FIG. 48 is a perspective view of the spacer of FIG. 47 showing the trigger wire in place.

The expansion mechanism for the spacer is integral with the device and disposed within the spacer body. In several embodiments, the expansion mechanism includes one or more expansion springs 50 disposed within the cage 13. While the spacer is inserted into the patient, each expansion spring 50 is held in a compressed state with a removable trigger wire 51 that temporarily secures the top and bottom plates together. The trigger wire 51 passes through a hook that is connected to or integral with the top plate 11 and into a notch 54 that is integral with the bottom plate 12. As shown in FIGS. 47-48, in one embodiment the trigger wire 51 passes through a hook 53 that extends from the top plate 11 and into a notch 54 in the stationary post 22 that extends from the bottom plate 12. In this way the trigger wire holds the top plate 11 and bottom plate 12 together as it runs through the hook connected to the top plate and into the notch integral with the bottom plate. In some embodiments the hook 53 is an aperture on the movable post 21 that extends from the top plate 11. Once the spacer is the desired position between the vertebrae, the user removes the trigger wire 51 by pulling it proximally releasing the top plate 11 from bottom plate 12. Then the expansion spring 50 pops the plates apart by instantly relaxing to the farthest extent possible in the intervertebral space, and expands until the top plate 11 is pushing on the top vertebrae and the bottom plate 12 is pushing on the bottom vertebrae. In this way that the plates 11, 12 are automatically separated the proper height in a single motion, without additional intervention.

In other embodiments, the expansion mechanism is a rotatable oval cam 60. See FIGS. 22-27. As the spacer is inserted into the patient, the long axis of the cam 60 remains parallel to the bottom plate 12. Once the spacer is in place, the cam 60 is rotated using a removable cam expansion tool inserted into a cam tool receiver 64. Rotating the cam 60 moves its long axis to an angle relative to the bottom plate, forcing the top plate 11 apart from the bottom plate 12. At maximum rotation, the long axis of the cam 60 is perpendicular to the bottom plate 12.

In other embodiments, the expansion mechanism is a rotatable link 70 of two obround link plates 71, 72 that are rotatably connected at one end with a rivet 73 or other fastener. See FIGS. 28-35. As the spacer 10 is inserted into the patient, the link plates are collapsed toward each other around the rivet. Once the spacer is in place, the link plates 71, 72 are rotated apart using a removable link expansion tool inserted into a link tool receiver 74. The free ends of the link 70 force the top plate 11 apart from the bottom plate 12.

Several specific embodiments of the device are described below. Other embodiments will be known to a person of skill in the art of intervertebral spacers.

FIGS. 1-5 show a first embodiment of the spacer with four locking mechanisms, two stanchions 20 at the distal end 14 and two stanchions 20 at the proximal end 15 of the spacer. A spring 55 biases the movable posts 21 against the stationary posts 22 in each stanchion 20. See FIGS. 4 and 5. The movable posts 21 abut the top plate 11 and slide along the top plate's lower surface 52.

The expansion mechanism of this first embodiment comprises two expansion springs 50, one at the distal end 14 of the device and one at the proximal end 15. When a user removes the trigger wire 51 from the compressed expansion springs, the expansion springs 50 instantly relax to the farthest extent possible in the intervertebral space, forcing the movable posts 21 apart from the stationary posts 22 in a linear sliding motion, permitting the posts 21, 22 and the steps to release from each other until the top plate 11 abuts the vertebra above it. The desired separation of the top and bottom plates is accomplished in a single motion without incrementally forcing the plates apart. The movable posts 21 and the stationary posts 22 then revert to an interlocking position and the plates are held apart at that distance by the locking mechanisms.

FIGS. 6-13 show a second embodiment of the spacer with two stanchions 20 at the distal end of the cage. The stanchions 20 are placed on either side of the expansion spring 50. See FIG. 9. A hinge 40 connects the top plate and bottom plate at the proximal end of the cage. The hinge 40 permits the distal end of the top plate 11 to lift relative to the bottom plate 12, while the proximal end of the top plate 11 remains at a constant distance from the bottom plate 12, thereby forming an angle between the vertebrae. A spring 55 forces the movable posts 51 against the stationary posts 22 in each stanchion 20 when spring is at rest.

The expansion mechanism of this second embodiment comprises a single expansion spring 50 at the distal end 14 of the device. When a user removes the trigger wire 51 from the compressed expansion spring 50, the expansion spring 50 instantly relaxes to the farthest extent possible in the intervertebral space, forcing the movable posts 21 from the stationary posts 22 in a rotary motion around a pivot point 56, permitting the posts 21, 22 and the steps to release from each other until the distal end of the top plate abuts the vertebra above it. The desired separation of the top and bottom plates is accomplished in a single motion without incrementally forcing the plates apart. The movable posts 21 and the stationary posts 22 then revert to an interlocking position and the plates are held apart at that distance by the locking mechanisms.

Figure 19:
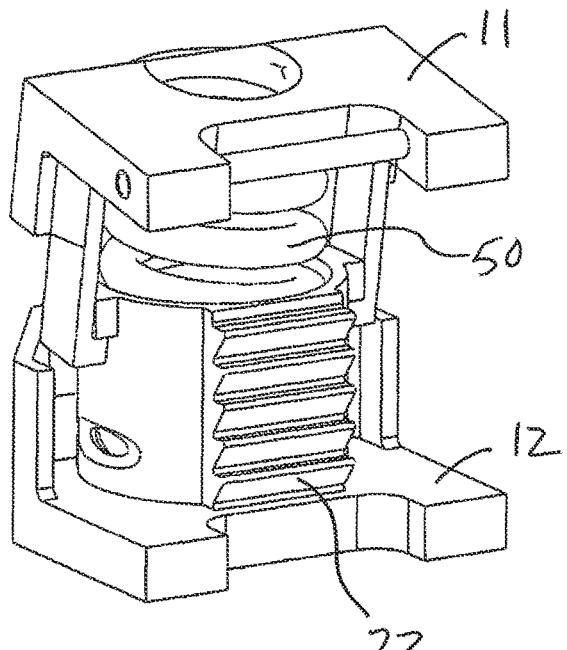
FIG. 19 is a side-perspective view of the spacer of FIG. 18.
Figure 20:
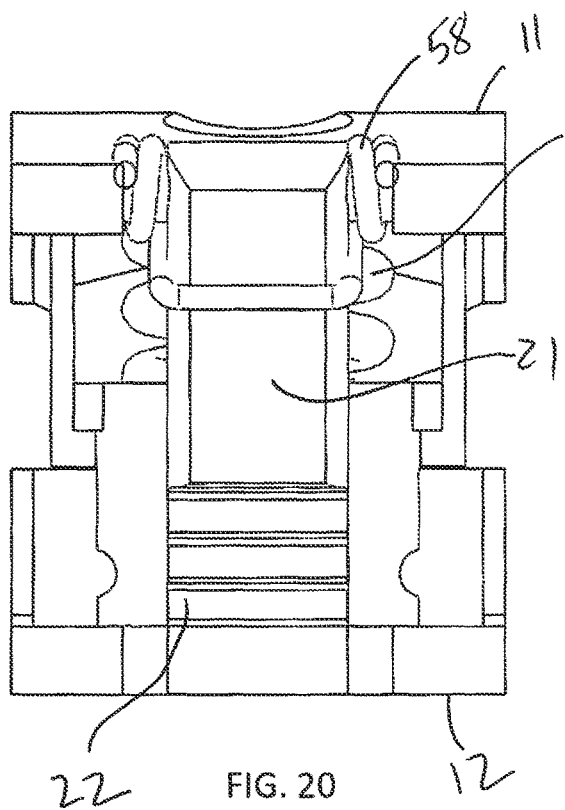
FIG. 20 is a cross-section view of the spacer of FIG. 14 along line D-D of FIG. 17.
Figure 21:
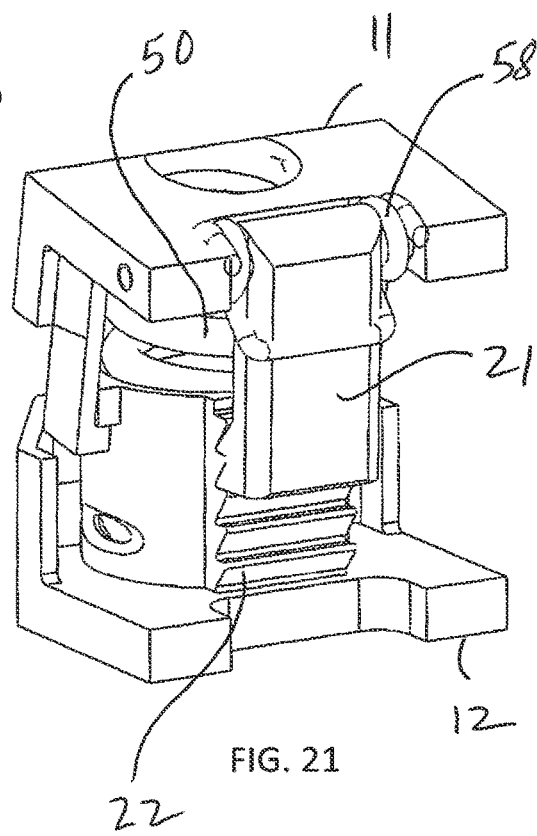
FIG. 21 is a side-perspective view of the spacer of FIG. 20.
Figure 22:
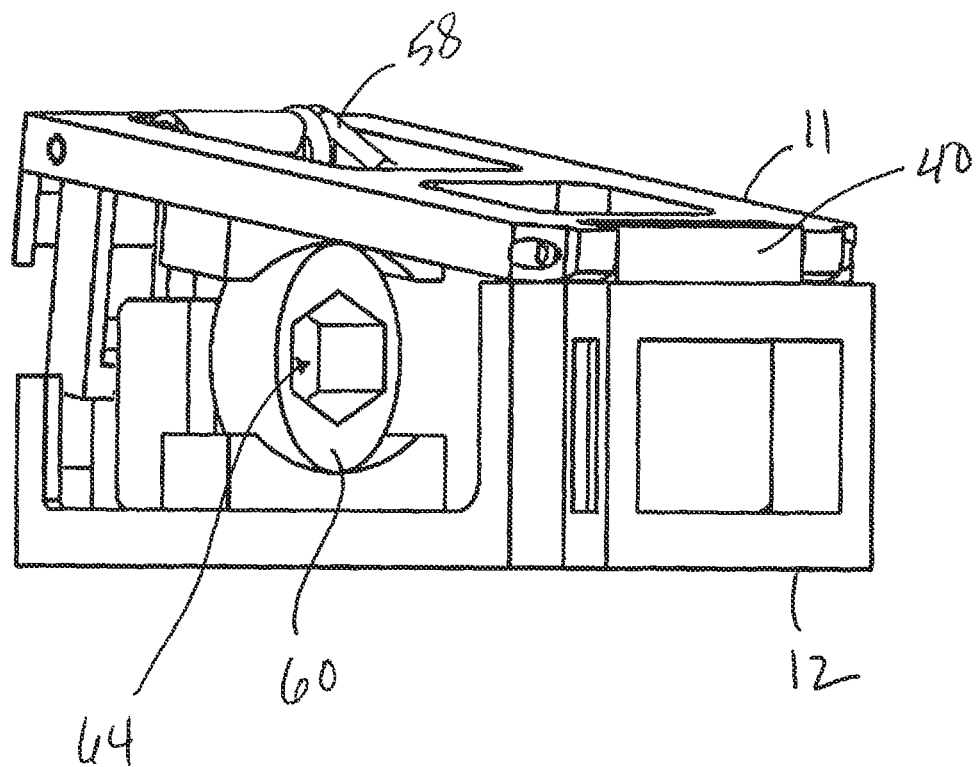
FIG. 22 is a rear perspective view of a fourth embodiment of a spacer in an expanded position.
Figure 23:
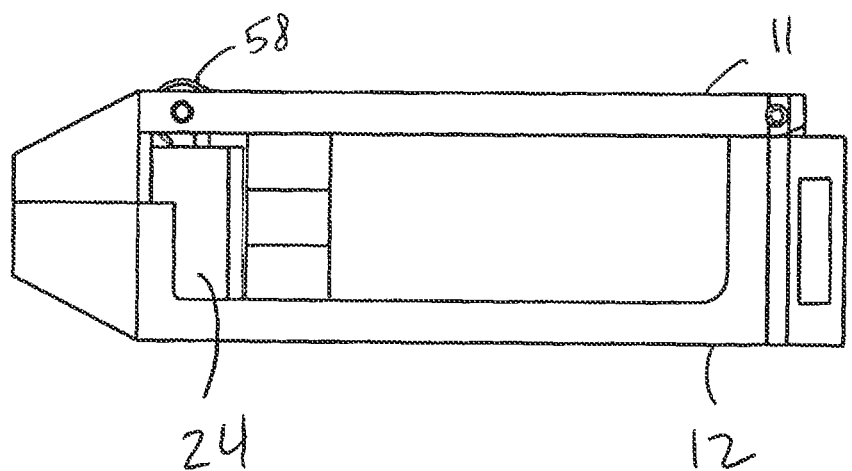
FIG. 23 is a side view of the spacer of FIG. 22 in an unexpanded position.
Figure 24:
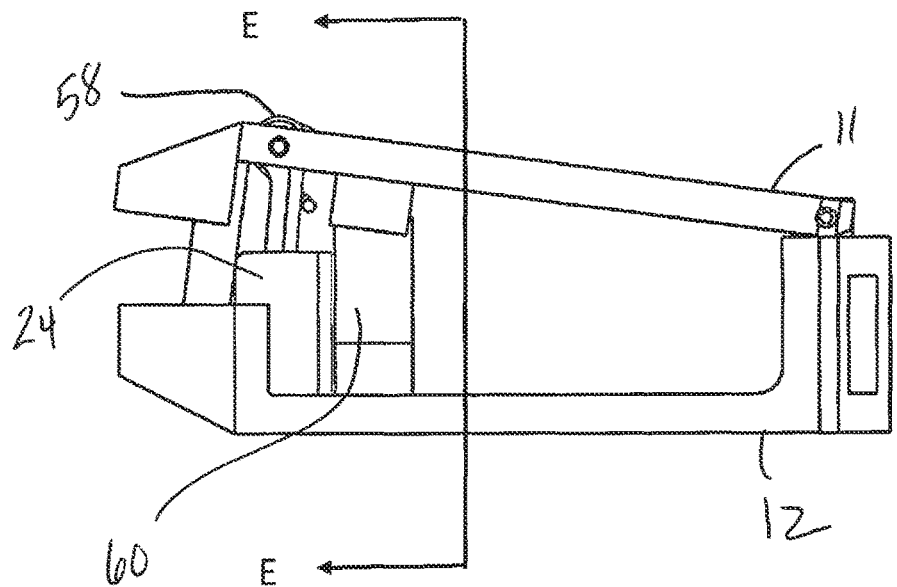
FIG. 24 is a side view of the spacer of FIG. 22 in an expanded position.
Figure 25:
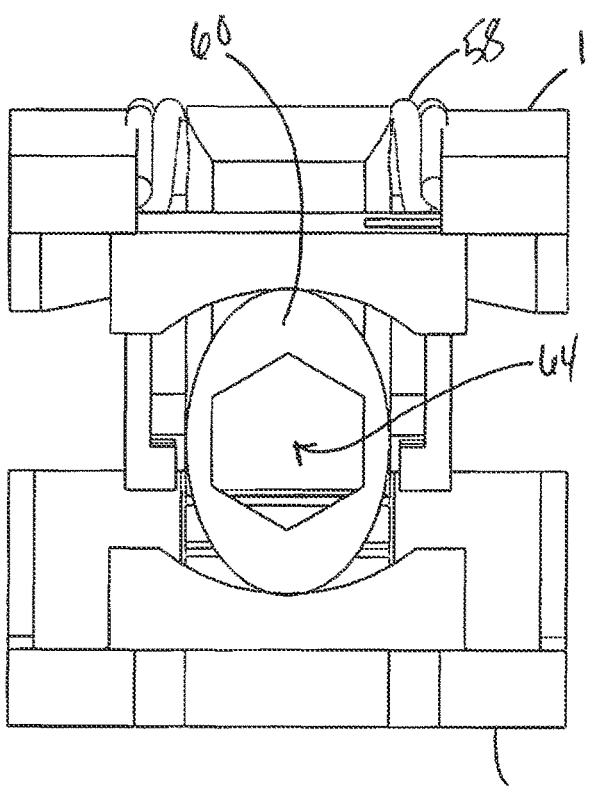
FIG. 25 is a cross-section view of the spacer of FIG. 22 along line E-E of FIG. 24 in an expanded position.
Figure 26:
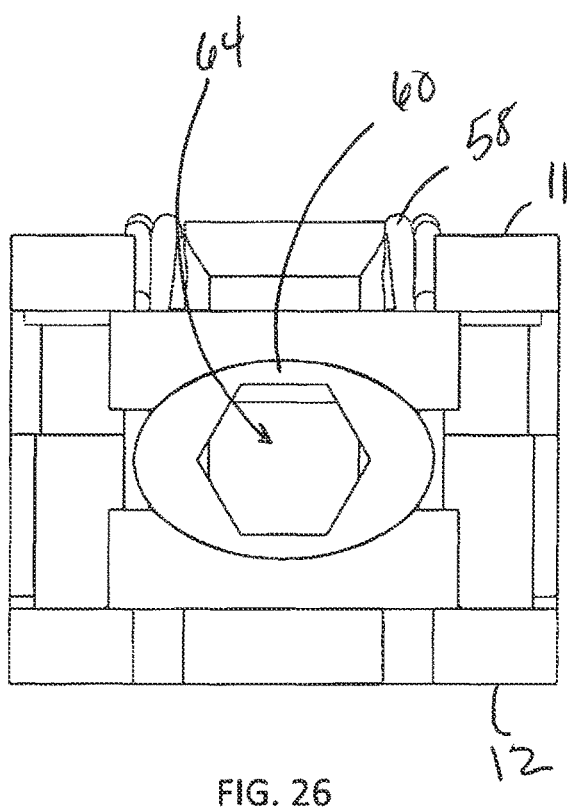
FIG. 26 is a cross-section view of the spacer of FIG. 22 along line E-E of FIG. 24 in an unexpanded position.
Figure 27:
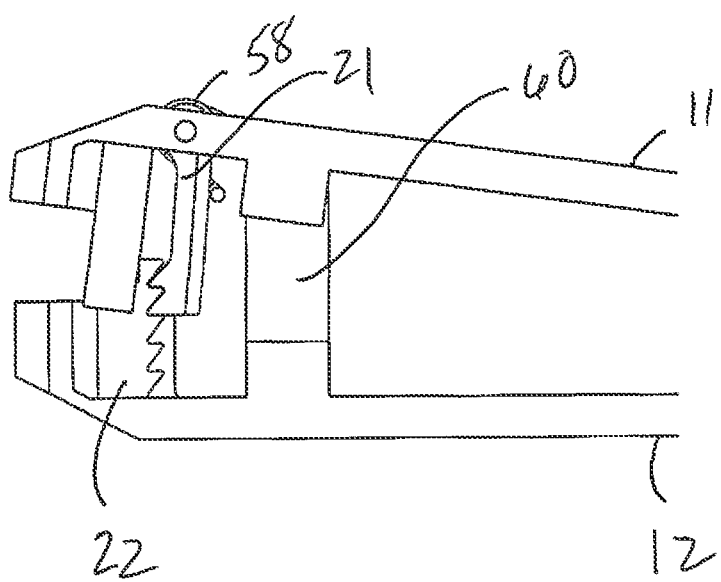
FIG. 27 is a partial side view of the spacer of FIG. 22 in an expanded position without the sheaths surrounding the steps.
Figure 28:
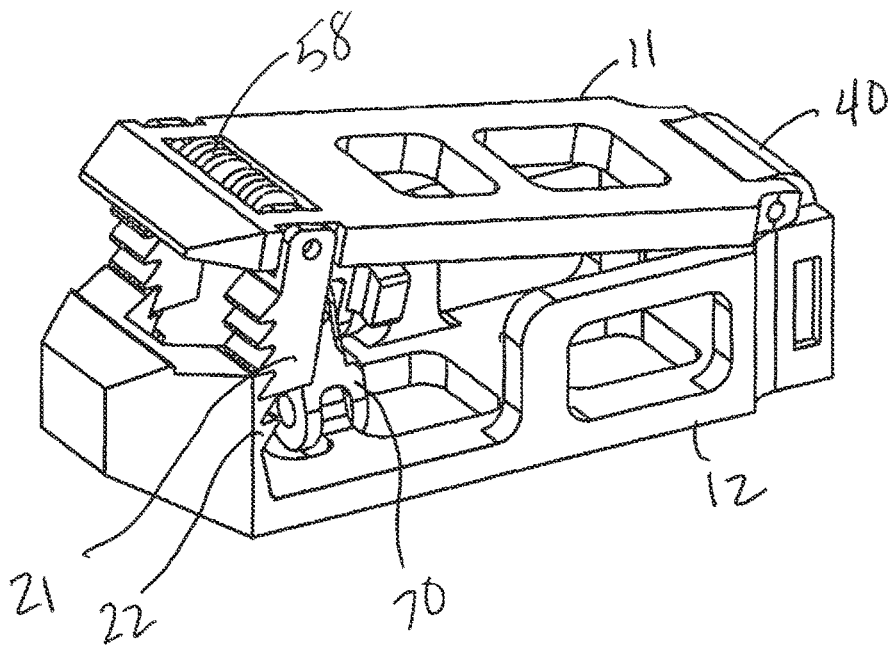
FIG. 28 is a rear perspective view of a fifth embodiment of a spacer in an expanded position.
Figure 29:
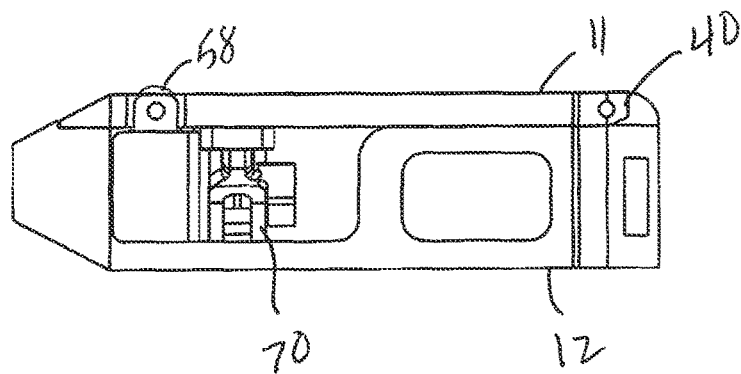
FIG. 29 is a side view of the spacer of FIG. 28 in an unexpanded position.
Figure 30:
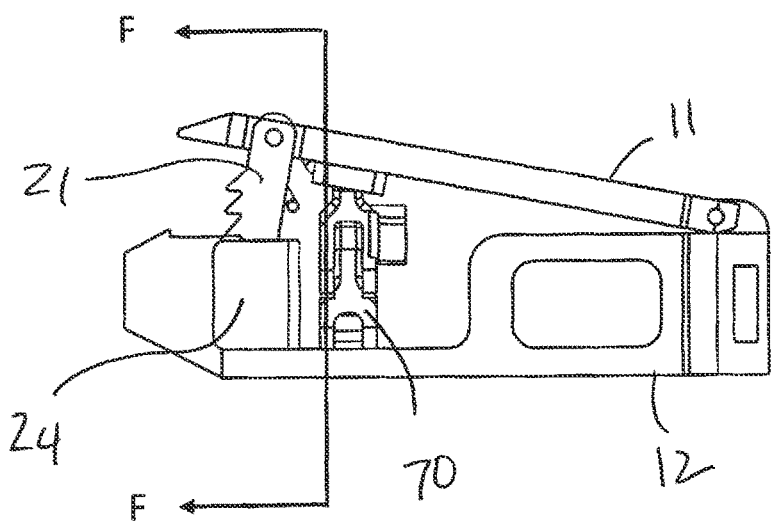
FIG. 30 is a side view of the spacer of FIG. 28 in an expanded position.
Figure 31:
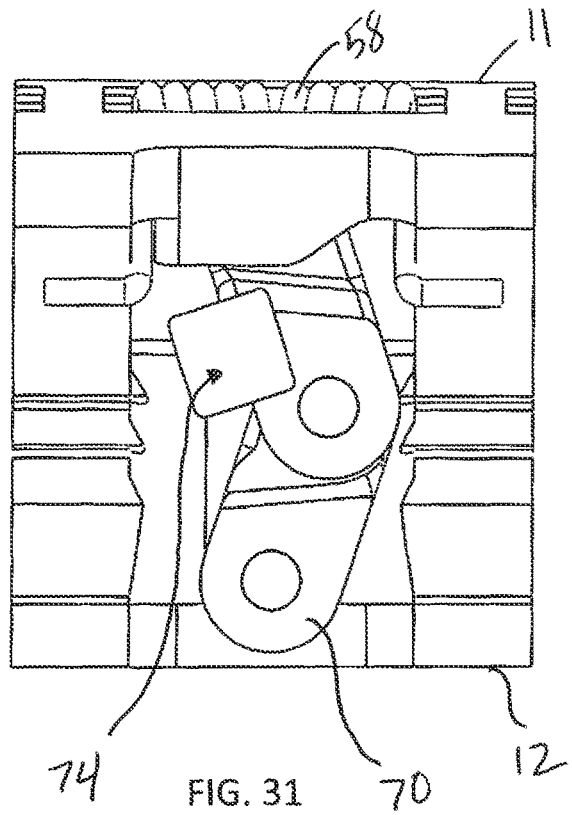
FIG. 31 is a cross-section view of the spacer of FIG. 28 along line F-F of FIG. 30 in an expanded position.
Figure 32:
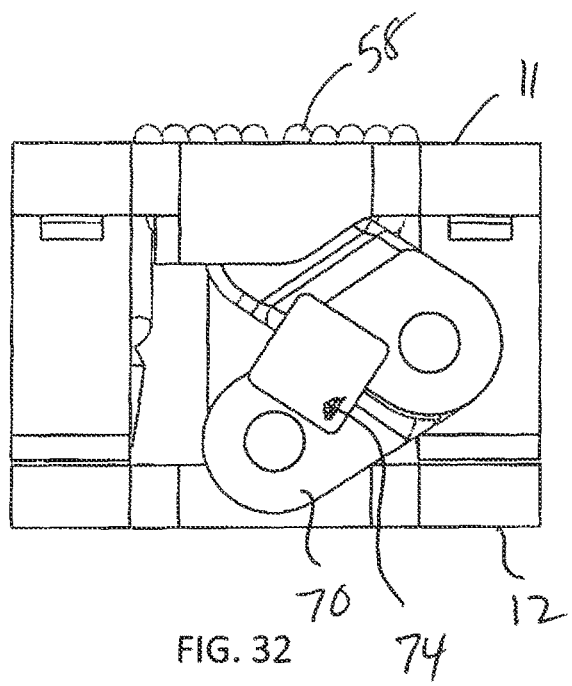
FIG. 32 is a cross-section view of the spacer of FIG. 28 along line F-F of FIG. 30 in an unexpanded position.
Figure 33:
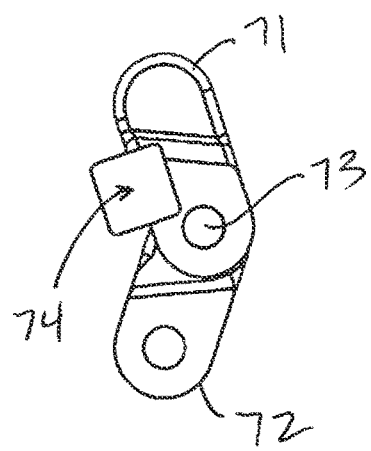
FIG. 33 is an isolated view of the link of FIG. 31 in an expanded position.
Figure 34:
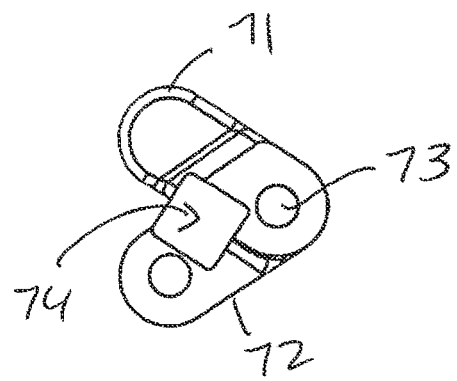
FIG. 34 is an isolated view of the link of FIG. 31 in an unexpanded position.
Figure 35:
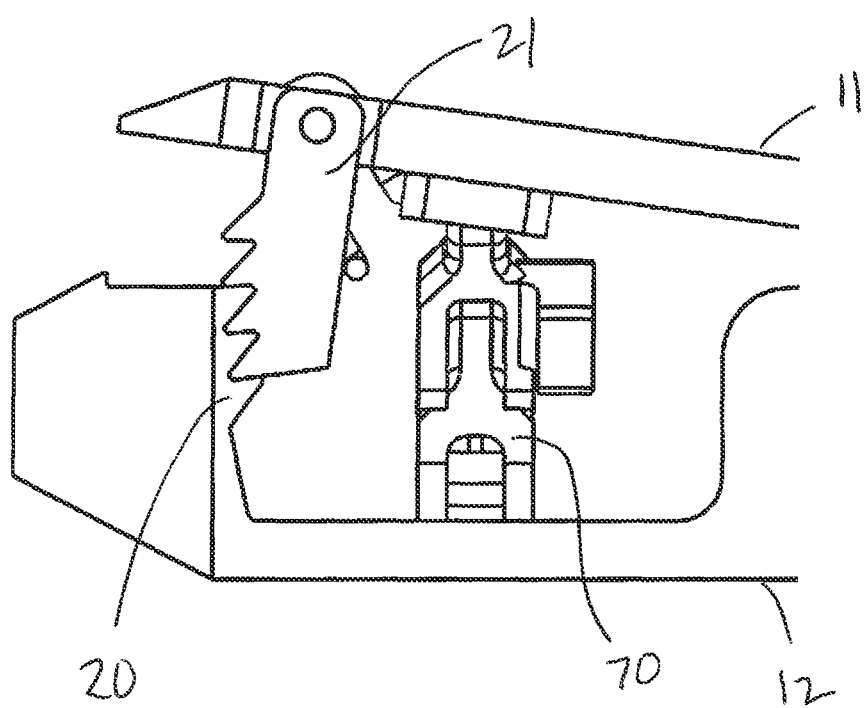
FIG. 35 is a partial side view of the spacer of FIG. 28.

FIGS. 14-21 show a third embodiment with a single stanchion 20. The single stanchion 20 is disposed within the cage, close to the expansion spring 50. FIG. 19 shows the single stanchion positioned in the cage between the expansion spring 50 and the proximal end of the cage, but the single stanchion 20 may instead be placed between the expansion spring 50 and the distal end of the cage. A hinge 40 connects the top plate and bottom plate at the proximal end of the cage. The hinge 40 permits the distal end of the top plate 11 to lift relative to the bottom plate 12, while the proximal end of the top plate 11 remains at a constant distance from the bottom plate 12, thereby forming an angle between the vertebrae. A torsion spring 58 forces the movable post 21 against the stationary posts 22 in the stanchion 20. When the compression spring 58 is compressed, the movable post 21 pivots away from the stationary post 22 about the long axis of the torsion spring.

The expansion mechanism of this third embodiment comprises a single expansion spring 50 at the distal end 14 of the device. When a user removes the trigger wire 51 from the compressed expansion spring 50, the expansion spring 50 instantly relaxes to the farthest extent possible in the intervertebral space, forcing the movable posts 21 from the stationary posts 22 in a rotary motion, permitting the posts 21, 22 and the steps to release from each other until the distal end of the top plate 11 abuts the vertebra above it. See FIG. 17. The desired separation of the top and bottom plates is accomplished in a single motion without incrementally forcing the plates apart. The movable posts 21 and the stationary posts 22 then revert to an interlocking position and the plates are held apart at that distance by the locking mechanisms.

FIGS. 22-27 show a fourth embodiment with a single locking mechanism at the distal end. A hinge 40 connects the top plate and bottom plate at the proximal end of the cage. The hinge 40 permits the distal end of the top plate 11 to lift relative to the bottom plate 12, while the proximal end of the top plate 11 remains at a constant distance from the bottom plate 12, thereby forming an angle between the vertebrae. A torsion compression spring 58 forces the movable post 21 against the stationary posts 22 in the stanchion 20 when the torsion spring is at rest. As the top and bottom plates are forced apart, the torsion springs are compressed and the posts are forced apart and unlocked. When the top and bottom plates are separated to the desired distance, the torsion springs relax, thus forcing the saw teeth of the posts to intermesh again, which locks the top and bottom plates apart at the desired distance.

The expansion mechanism of this fourth embodiment comprises a rotatable oval cam 60. To lift the distal end of the top plate 11, a removable cam expansion tool is inserted into a cam tool receiver 64 and rotated, thereby causing the long axis of the cam to move against the top plate 11 and forcing the top plate 11 apart from the bottom plate 12. Once the top plate 11 is at the desired angle, the user removes the cam expansion tool from the patient.

FIGS. 28-35 show a fifth embodiment with two locking mechanisms at the distal end. The proximal end uses a hinge 40 to permit the distal end of the top plate 11 to lift relative to the bottom plate 12, while the proximal end of the top plate 11 remains at a constant distance from the bottom plate 12, thereby forming an angle between the vertebrae. A torsion spring 58 forces the movable post 21 against the stationary posts 22 in the stanchion 20. As the top and bottom plates are forced apart, the torsion springs are compressed and the posts are forced apart and unlocked. When the top and bottom plates are separated to the desired distance, the torsion springs relax, thus forcing the saw teeth of the posts to intermesh again, which locks the top and bottom plates apart at the desired distance.

The expansion mechanism of this fifth embodiment comprises a rotatable link assembly 70. To lift the distal end of the top plate 11, a removable link expansion tool is inserted into a link tool receiver 74 and rotated, thereby causing the link plates to open up forcing the top plate 11 apart from the bottom plate 12. Once the top plate 11 is at the desired angle, the user removes the link expansion tool from the patient.

While there has been illustrated and described what is at present considered to be the preferred embodiments of the present invention, it will be understood by those skilled in the art that various changes and modifications may be made and equivalents may be substituted for elements thereof without departing from the true scope of the invention. Therefore, it is intended that this invention not be limited to the particular embodiments disclosed, but that the invention will include all embodiments falling within the scope of the appended claims.

The invention claimed is:

1. An expandable intervertebral spacer system, the spacer system comprising:
   a top plate and a bottom plate forming a cage surrounding a cavity, wherein the cage has a proximal end and a distal end;
   one or more locking mechanisms that locks the top plate and the bottom plate apart a desired distance, wherein each locking mechanism comprises:
      a stanchion comprising a movable post having saw teeth and a stationary post having saw teeth; and
      a spring configured to bias the movable post against the stationary post, such that the movable post and stationary post cooperate to lock the top plate and bottom plate apart the desired distance; and
   an expansion mechanism integral with the cage, wherein the expansion mechanism comprises one or more expansion springs and wherein the one or more expansion springs is held in a compressed state with a removable trigger wire.

2. The expandable intervertebral spacer system according to claim 1 wherein the trigger wire runs through a hook integral with or connected to the top plate and into a notch integral with the bottom plate such that the top plate and bottom plate are held together.

3. The expandable intervertebral spacer system according to claim 1 wherein the expansion mechanism comprises a rotatable cam or a rotatable link.

4. The expandable intervertebral spacer system according to claim 3 further comprising a removable insertion tool insertable into the cavity from the proximal end of the cage, wherein the insertion tool is configured to operate the expansion mechanism which forces the top plate and bottom plate apart.

5. The expandable intervertebral spacer system according to claim 1 wherein:
   each of the saw teeth has a horizontal edge;
   the horizontal edge of the saw teeth on the stationary post are at an angle greater than 90 degrees to the stationary post; and
   the horizontal edge of the saw teeth on the movable post are at an angle to the movable post that is complementary to the saw teeth on the stationary post.

6. An expandable intervertebral spacer system, the spacer system comprising:
   a top plate and a bottom plate forming a cage surrounding a cavity, wherein the cage has a proximal end and a distal end;
   a locking mechanism that locks the top plate and the bottom plate apart a desired distance, wherein the locking mechanism comprises:
      a stanchion comprising a movable post having saw teeth and a stationary post having saw teeth; and
      a spring configured to bias the movable post against the stationary post, such that the movable post and stationary post cooperate to lock the top plate and bottom plate apart the desired distance; and
   a first expansion spring integral with the cage at the distal end of the cage,
   wherein the first expansion spring is held in a compressed state with a removable trigger wire.

7. The expandable intervertebral spacer system according to claim 6 wherein the locking mechanism is positioned in the cage between the first expansion spring and the proximal end of the cage.

8. The expandable intervertebral spacer system according to claim 6 further comprising a second expansion spring disposed at the proximal end of the cage wherein:
   the cage is moveable between a collapsed configuration and an expanded configuration; and
   in the expanded configuration the top plate and bottom plate are parallel.

9. The expandable intervertebral spacer system according to claim 8 wherein the first expansion spring and second expansion spring are held in a compressed state with the removable trigger wire.

10. The expandable intervertebral spacer system according to claim 6 further comprising a hinge connecting the top plate and bottom plate at the proximal end of the cage, wherein
   the cage is moveable between a collapsed configuration and an expanded configuration; and
   wherein in the expanded configuration the top plate and bottom plate are not parallel.

11. The expandable intervertebral spacer system according to claim 6 wherein:
   each of the saw teeth has a horizontal edge;
   the horizontal edge of the saw teeth on the stationary post are at an angle greater than 90 degrees to the stationary post; and the horizontal edge of the saw teeth on the movable post are at an angle to the movable post that is complementary to the saw teeth on the stationary post.

12. An expandable intervertebral spacer system, the spacer system comprising:
 a top plate and a bottom plate forming a cage surrounding a cavity, wherein the cage has a proximal end and a distal end;
 a locking mechanism that locks the top plate and the bottom plate apart a desired distance, wherein the locking mechanism further comprises:
  a stanchion comprising a movable post having saw teeth and a stationary post having saw teeth; and
  a spring configured to bias the movable post against the stationary post, such that the movable post and stationary post cooperate to lock the top plate and bottom plate apart the desired distance;
 a first expansion spring integral with the cage at the distal end of the cage; and
 a trigger wire that runs through a hook connected to or integral with the top plate and into a notch integral with the bottom plate such that the top plate and bottom plate are held together.

13. The expandable intervertebral spacer system according to claim 12 wherein:
 each of the saw teeth has a horizontal edge;
 the horizontal edge of the saw teeth on the stationary post are at an angle greater than 90 degrees to the stationary post; and
 the horizontal edge of the saw teeth on the movable post are at an angle to the movable post that is complementary to the saw teeth on the stationary post.

14. An expandable intervertebral spacer system, the spacer system comprising:
 a top plate and a bottom plate forming a cage surrounding a cavity, wherein the cage has a proximal end and a distal end;
 two locking mechanisms that lock the top plate and the bottom plate apart a desired distance, wherein each locking mechanism further comprises:
  a stanchion comprising a movable post having saw teeth and a stationary post having saw teeth; and
  a spring configured to bias the movable post against the stationary post, such that the movable post and stationary post cooperate to lock the top plate and bottom plate apart the desired distance; and
 a first expansion spring integral with the cage at the distal end of the cage.

15. The expandable intervertebral spacer system according to claim 14 wherein the first expansion spring is held in a compressed state with a removable trigger wire.

16. The expandable intervertebral spacer system according to claim 11 wherein the trigger wire runs through a hook connected to or integral with the top plate and into a notch integral with the bottom plate such that the top plate and bottom plate are held together.

17. The expandable intervertebral spacer system according to claim 16 wherein:
 the cage is moveable between a collapsed configuration and an expanded configuration; and
 in the expanded configuration the top plate and bottom plate are parallel.

18. The expandable intervertebral spacer system according to claim 16 further comprising a hinge connecting the top plate and bottom plate at the proximal end of the cage, wherein:
 the cage is moveable between a collapsed configuration and an expanded configuration; and
 in the expanded configuration the top plate and bottom plate are not parallel.

19. The expandable intervertebral spacer system according to claim 14 wherein:
 the cage is moveable between a collapsed configuration and an expanded configuration; and
 in the expanded configuration the top plate and bottom plate are parallel.

20. The expandable intervertebral spacer system according to claim 14 further comprising a hinge connecting the top plate and bottom plate at the proximal end of the cage, wherein:
 the cage is moveable between a collapsed configuration and an expanded configuration; and
 in the expanded configuration the top plate and bottom plate are not parallel.

21. An expandable intervertebral spacer system, the spacer system comprising:
 a top plate and a bottom plate forming a cage surrounding a cavity, wherein the cage has a proximal end and a distal end;
 a locking mechanism within the cavity and integral with the cage, wherein the locking mechanism is configured to lock the top plate and bottom plate apart a desired distance, wherein each locking mechanism comprises:
  a stanchion comprising a movable post having saw teeth and a stationary post having saw teeth; and
  a spring configured to bias the movable post against the stationary post, such that the movable post and stationary post cooperate to lock the top plate and bottom plate apart the desired distance; and
 an expansion mechanism within the cavity and integral with the cage, wherein the expansion mechanism is configured to force the top plate apart from the bottom plate a desired distance in a single motion, wherein the expansion mechanism comprises:
  a first expansion spring at the distal end of the cage; and
  a trigger wire,
  wherein the first expansion spring and the trigger wire cooperate such that if the trigger wire is removed from the first expansion spring, the first expansion spring relaxes to the farthest extent possible in an intervertebral space.

* * * * *